(12) United States Patent
Whitcup et al.

(10) Patent No.: US 9,233,071 B2
(45) Date of Patent: *Jan. 12, 2016

(54) METHODS FOR TREATING RETINOPATHY WITH EXTENDED THERAPEUTIC EFFECT

(71) Applicant: Allergan, Inc., Irvine, CA (US)

(72) Inventors: Scott M. Whitcup, Laguna Hills, CA (US); David A. Weber, Danville, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/541,520

(22) Filed: Nov. 14, 2014

(65) Prior Publication Data

US 2015/0133559 A1    May 14, 2015

Related U.S. Application Data

(63) Continuation of application No. 14/306,363, filed on Jun. 17, 2014, now Pat. No. 8,911,768, which is a continuation of application No. 13/946,294, filed on Jul. 19, 2013, now Pat. No. 8,802,129, which is a continuation of application No. 13/604,809, filed on Sep. 6, 2012, now abandoned, which is a continuation of application No. 11/292,544, filed on Dec. 2, 2005, now abandoned, which is a continuation-in-part of application No. 10/837,357, filed on Apr. 30, 2004, now abandoned.

(51) Int. Cl.

| A61K 9/00 | (2006.01) |
|---|---|
| A61K 31/56 | (2006.01) |
| A61K 31/57 | (2006.01) |
| A61K 47/34 | (2006.01) |
| A61K 39/395 | (2006.01) |
| A61F 9/00 | (2006.01) |
| A61K 9/16 | (2006.01) |
| C07K 16/18 | (2006.01) |
| C07K 16/22 | (2006.01) |
| A61K 31/165 | (2006.01) |

(52) U.S. Cl.
CPC ............ *A61K 9/0051* (2013.01); *A61F 9/0017* (2013.01); *A61K 9/0024* (2013.01); *A61K 9/1647* (2013.01); *A61K 31/165* (2013.01); *A61K 31/56* (2013.01); *A61K 31/57* (2013.01); *A61K 39/3955* (2013.01); *A61K 47/34* (2013.01); *C07K 16/18* (2013.01); *C07K 16/22* (2013.01)

(58) Field of Classification Search
None
See application file for complete search history.

(56) References Cited

U.S. PATENT DOCUMENTS

| 3,416,530 A | 12/1968 | Ness |
|---|---|---|
| 3,432,592 A | 3/1969 | Speiser |
| 3,845,770 A | 11/1974 | Theeuwes et al. |
| 3,914,402 A | 10/1975 | Shell |
| 3,916,899 A | 11/1975 | Theeuwes et al. |
| 3,921,632 A | 11/1975 | Bardani |
| 3,961,628 A | 6/1976 | Arnold |
| 3,986,510 A | 10/1976 | Higuchi et al. |
| 4,008,864 A | 2/1977 | Torphammar et al. |
| 4,014,334 A | 3/1977 | Theeuwes et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,180,646 A | 12/1979 | Choi et al. |
| 4,186,184 A | 1/1980 | Zaffaroni |
| 4,200,098 A | 4/1980 | Ayer et al. |
| 4,201,210 A | 5/1980 | Hughes et al. |
| 4,285,987 A | 8/1981 | Ayer et al. |
| 4,300,557 A | 11/1981 | Refojo et al. |
| 4,304,765 A | 12/1981 | Shell et al. |
| 4,327,725 A | 5/1982 | Cortese et al. |
| 4,402,979 A | 9/1983 | Shen et al. |
| 4,451,254 A | 5/1984 | Dinius et al. |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,668,506 A | 5/1987 | Bawa |
| 4,756,911 A | 7/1988 | Drost et al. |
| 4,801,460 A | 1/1989 | Goertz et al. |
| 4,806,337 A | 2/1989 | Snipes et al. |
| 4,853,224 A | 8/1989 | Wong |
| 4,863,457 A | 9/1989 | Lee |
| 4,865,846 A | 9/1989 | Kaufman |
| 4,945,089 A | 7/1990 | Clark |
| 4,959,217 A | 9/1990 | Sanders et al. |

(Continued)

FOREIGN PATENT DOCUMENTS

| CA | 1333770 | 10/1988 |
|---|---|---|
| CA | 2336703 | 1/2000 |

(Continued)

OTHER PUBLICATIONS

Cantor, Louis B.; Expert Opinion on Investigational Drugs; (2001) 10(4); pp. 721-731.*

(Continued)

*Primary Examiner* — Jeffrey T Palenik

(74) *Attorney, Agent, or Firm* — Brigitte C. Phan; Ted A. Chan; Debra D. Condino

(57) ABSTRACT

Methods for treating and preventing ocular conditions by administering an compound to the vitreous chamber of a patient at risk of, or suffering from, the ocular condition.

8 Claims, 3 Drawing Sheets

(56) References Cited

U.S. PATENT DOCUMENTS

| | | | |
|---|---|---|---|
| 4,997,652 A | 3/1991 | Wong | |
| 5,004,601 A | 4/1991 | Snipes | |
| 5,004,614 A | 4/1991 | Staniforth | |
| 5,006,342 A | 4/1991 | Cleary et al. | |
| 5,019,400 A | 5/1991 | Gombotz et al. | |
| 5,028,624 A | 7/1991 | Chan et al. | |
| 5,034,413 A | 7/1991 | Chan et al. | |
| 5,075,115 A | 12/1991 | Brine | |
| 5,082,655 A | 1/1992 | Snipes et al. | |
| 5,164,188 A | 11/1992 | Wong | |
| 5,169,638 A | 12/1992 | Dennis et al. | |
| 5,268,178 A | 12/1993 | Calhoun et al. | |
| 5,314,419 A | 5/1994 | Pelling | |
| 5,322,691 A | 6/1994 | Darougar et al. | |
| 5,356,629 A | 10/1994 | Sander et al. | |
| 5,378,475 A | 1/1995 | Smith et al. | |
| 5,384,333 A | 1/1995 | Davis et al. | |
| 5,385,887 A | 1/1995 | Yim et al. | |
| 5,443,505 A | 8/1995 | Wong et al. | |
| 5,446,041 A | 8/1995 | Chan et al. | |
| 5,476,511 A | 12/1995 | Gwon et al. | |
| 5,501,856 A | 3/1996 | Ohtori et al. | |
| 5,574,066 A | 11/1996 | Chan et al. | |
| 5,597,897 A | 1/1997 | Ron et al. | |
| 5,601,844 A | 2/1997 | Kagayama et al. | |
| 5,656,297 A | 8/1997 | Bernstein et al. | |
| 5,660,847 A | 8/1997 | Magruder et al. | |
| 5,660,851 A | 8/1997 | Domb | |
| 5,688,819 A | 11/1997 | Woodward et al. | |
| 5,693,335 A | 12/1997 | Xia et al. | |
| 5,707,643 A | 1/1998 | Ogura | |
| 5,755,785 A | 5/1998 | Rowsey et al. | |
| 5,766,242 A | 6/1998 | Wong et al. | |
| 5,773,019 A | 6/1998 | Ashton et al. | |
| 5,773,021 A | 6/1998 | Gurtler et al. | |
| 5,824,072 A | 10/1998 | Wong | |
| 5,824,074 A | 10/1998 | Koch | |
| 5,869,079 A | 2/1999 | Wong et al. | |
| 5,882,682 A | 3/1999 | Rork et al. | |
| 5,902,598 A | 5/1999 | Chen et al. | |
| 5,941,250 A | 8/1999 | Aramant et al. | |
| 5,962,027 A | 10/1999 | Hughes | |
| 5,972,369 A | 10/1999 | Roorda et al. | |
| 6,045,791 A | 4/2000 | Liu | |
| 6,046,187 A | 4/2000 | Berde et al. | |
| 6,051,576 A | 4/2000 | Ashton et al. | |
| 6,063,116 A | 5/2000 | Kelleher | |
| 6,074,661 A | 6/2000 | Olejnik et al. | |
| 6,217,895 B1 | 4/2001 | Guo et al. | |
| 6,217,911 B1 | 4/2001 | Vaugn et al. | |
| 6,309,669 B1 | 10/2001 | Setterstrom et al. | |
| 6,329,369 B1 | 12/2001 | Chow et al. | |
| 6,331,313 B1 | 12/2001 | Wong et al. | |
| 6,369,116 B1 | 4/2002 | Wong et al. | |
| 6,403,649 B1 | 6/2002 | Woodward et al. | |
| 6,497,729 B1 | 12/2002 | Moussy et al. | |
| 6,534,542 B2 | 3/2003 | Chow et al. | |
| 6,537,568 B2 | 3/2003 | Olejnik et al. | |
| 6,545,182 B2 | 4/2003 | Chow et al. | |
| 6,548,078 B2 | 4/2003 | Guo et al. | |
| 6,699,493 B2 | 3/2004 | Wong | |
| 6,713,081 B2 | 3/2004 | Robinson et al. | |
| 6,726,918 B1 | 4/2004 | Wong et al. | |
| 6,841,684 B2 | 1/2005 | Chow et al. | |
| 7,048,946 B1 | 5/2006 | Wong et al. | |
| 7,091,232 B2 | 8/2006 | Chow et al. | |
| 7,141,597 B2 | 11/2006 | Chow et al. | |
| 7,276,522 B2 | 10/2007 | Heidelbaugh et al. | |
| 7,335,803 B2 | 2/2008 | Chow et al. | |
| 2004/0019098 A1 | 1/2004 | Andrews et al. | |
| 2004/0132824 A1 | 7/2004 | Gil et al. | |
| 2004/0137059 A1 | 7/2004 | Nivaggioli et al. | |
| 2004/0151753 A1 | 8/2004 | Chen | |
| 2004/0170665 A1 | 9/2004 | Donovan | |
| 2004/0266776 A1 | 12/2004 | Gil et al. | |
| 2005/0048099 A1 | 3/2005 | Shiah et al. | |
| 2005/0058696 A1 | 3/2005 | Donello et al. | |
| 2005/0059664 A1 | 3/2005 | Gil et al. | |
| 2005/0059744 A1 | 3/2005 | Donello et al. | |
| 2005/0101582 A1 | 5/2005 | Lyons et al. | |
| 2005/0181017 A1 | 8/2005 | Hughes et al. | |
| 2005/0232966 A1 | 10/2005 | Hughes et al. | |
| 2005/0244464 A1 | 11/2005 | Hughes et al. | |
| 2005/0244469 A1 | 11/2005 | Whitcup et al. | |
| 2005/0244474 A1 | 11/2005 | Huang et al. | |
| 2006/0009498 A1 | 1/2006 | Whitcup | |
| 2006/0233859 A1 | 10/2006 | Whitcup et al. | |
| 2007/0224246 A1 | 9/2007 | Hughes et al. | |
| 2007/0298073 A1 | 12/2007 | Whitcup et al. | |
| 2012/0035148 A1 | 2/2012 | Whitcup | |

FOREIGN PATENT DOCUMENTS

| | | |
|---|---|---|
| DE | 430539 | 6/1991 |
| DE | WO91/15495 | 10/1991 |
| DE | 488401 | 6/1992 |
| DE | 654256 | 5/1995 |
| EP | 0 052 916 | 7/1981 |
| EP | 0 102 265 | 3/1984 |
| EP | 0 197 718 | 3/1986 |
| EP | 0 322 319 | 6/1989 |
| EP | 0 364 417 | 9/1989 |
| EP | 0 474 098 | 3/1992 |
| EP | 0 311 065 | 10/1998 |
| EP | 0 992 244 | 4/2000 |
| WO | WO91/18940 | 12/1991 |
| WO | WO92/21660 A1 | 12/1992 |
| WO | WO 93/10141 | 5/1993 |
| WO | WO94/03427 A1 | 2/1994 |
| WO | WO94/10202 A1 | 5/1994 |
| WO | WO94/14808 A1 | 7/1994 |
| WO | WO 94/18956 | 9/1994 |
| WO | WO95/13765 | 5/1995 |
| WO | WO 96/38174 | 12/1996 |
| WO | WO 97/26869 | 7/1997 |
| WO | WO 98/22130 | 5/1998 |
| WO | WO 99/11244 | 3/1999 |
| WO | WO 00/02564 | 1/2000 |
| WO | WO 00/37056 | 6/2000 |
| WO | WO 00/56340 | 9/2000 |
| WO | WO 00/62760 | 10/2000 |
| WO | WO 01/30323 | 5/2001 |
| WO | WO02/02076 A | 1/2002 |
| WO | WO 02/43785 | 6/2002 |
| WO | WO 03/094888 | 5/2003 |
| WO | WO 2004/026106 | 9/2003 |
| WO | WO2004/062649 A | 7/2004 |
| WO | WO2005/013206 | 4/2005 |
| WO | WO 2005/110362 | 4/2005 |
| WO | WO2005/024897 | 7/2005 |
| WO | WO 2006/093758 | 9/2006 |
| WO | WO 2007/130945 | 11/2007 |

OTHER PUBLICATIONS

Bloch-Michel E. (1992), *Opening Address: intermediate uveitis*, In Intermediate Uveitis, Dev. Opthalmol, W.R.F. Böke et al. editors., Basel: Karger, 23:1-2.

Bodor, N. et al. (1992), *A Comparison of intraocular pressure elevating activity of loteprednol etabonate and dexamethasone in rabbits*, Current Eye Research 11:525-30.

Böke, W. (1992), *Clinical picture of Intermediate uveitis*, In Intermediate Uveitis, Dev. Opthalmol. W.R.F. Böke et al, editors., Basel: Karger, 23:20-7.

CDER Application No. 22-315 for Posurdex; (last signed on May 1, 2009); 26 pp.; retrieved Mar. 15, 2012.

Cheng C-K et al. (1995). *Intravitreal sustained-release dexamethasone device in the treatment of experimental uveitis*, Invest. Opthalmol. Vis. Sci. 36:442-53.

Dohlman C. et al., *Treatment of corneal edema with a buried implant*, Tr. Am. Acad. Opth. & Otol., Mar.-Apr. 1966, pp. 267-280.

(56) References Cited

OTHER PUBLICATIONS

Enyedi, Laura B. et al., *An intravitreal device providing sustained release of cyclosporine and dexamethasone*, Current Eye Research, Oct. 17, 1995, pp. 549-557.
Gillies, M.C., et al., Safety of an intravitreal Injection of triamcinolone, Arch Opthalmol, vol. 122, Mar. 2004, pp. 336-340.
Hainsworth, Dean P. et al., *Sustained Release Intravitreal Dexamethasone*, Journal of Ocular Pharmacology and Therapeutics, vol. 12, No. 1, 1996, pp. 57-63.
Helier, *Biodegradable Polymers in Controlled Drug Delivery*, In: "CRC Critical Reviews in Therapeutic Drug Carrier Systems," vol. 1, Issue 1, CRC Press, Boca Raton, FL (1987), pp. 39-90.
Jonas, J. B., et al., Intraocular pressure after intravitreal injection of triamcinolone acetonide, Br J Opthalmol 2003, 87: pp. 24-27.
Kendall & Thomas, 1994, Proc. Nat'l Acad. Sci 90: 10705-08.
Kim, et al, 1993, Nature 362: 841-844), RNA ligands (Jellinak, et al, Biochemistry 33: 10450-56).
Kinselia, et al, 1992, Exp. Cell Res. 199 : 56-62.
Kochinke, F. et al., *Biodegradable Drug Delivery System for Uveitis Treatment*, Investigative Opthalmology & Visual Science, Feb. 15, 1996, vol. 37, No. 3, 186-398, Abstract.
Lee, V.H.L. et al. (1989), *Drug delivery to the posterior segment* Chapter 25 in Retina. T.E. Ogden and A.P. Schachat eds., St. Louis: CV Mosby, vol. 1, pp. 483-498.
Marcon, I., *A double-masked comparison of betaxolol and levobunolol for the treatment of primary open-angle glaucoma*, Arq Bras Oftalmol 1990; 53(1):27-32.
Mariani, et al, 1994, Proc. Am. Assoc. Cancer Res. 35:2268).
Maurice, D.M. (1983), *Micropharmaceutics of the eye*, Ocular Inflammation Ther. 1:97-102.
Molfino, F., et al., *IOP-lowering effect of dorzolamide 2% versus brimonidine tartrate 0.2%, A prospective randomized cross over study*, Invest Opthalmol Vis Sci Mar. 15, 1998;39(4):S481.
Morita Y., et al., *Intravitreous delivery of dexamethasone sodium m-sulfobenzoate from poly(DL-lactic acid) implants*, Biol. Pharm. Bull., Feb. 1998;21(2): 188-90.
Nakamura O., et al., *Inhibition of neovascularization and tumor growth by dexamethasone*, No To Shinkel, Jan. 1992;44(1):37-41.
Olsen, T.W. et al. (1995), *Human clera permeability: effects of age, cryotherapy, transscleral diode laser, and surgical thinning*, Invest, Ophthalmol. Vis. Sci. 36:1893-1903.
Rao, N.A. et al.; Pinar, V., et al. (1997), *Intraocular Inflammation and uveitis* In Basic and Clinical Science Course. Section 9 (1997-1998) San Francisco: American Academy of Ophthalmology, pp. 57-80, 102-103, 152-156.
Renfro, L. et al. (1992). *Ocular Clinics of topical and systemic steriods*, Dermatologic Clinics 10:505-12.
Sasaki et al.; "Progress in Retinal and Eye Research", vol. 15, No. 2; Chapter 11: Delivery of Drugs to the Eye by Topical Application; (see section 2.3); pp. 583-620, dated 1996.
Schwartz, B. (1966). *The response of ocular pressure to corticosteroids*, Ophthalmol. Clin. North Am. 6:929-89.
Skalka, H.W. et al. (1980). *Effect of corticosteroids on cataract formation*, Arch Ophthalmol 98:1773-7.
Stewart, W. et al. *Washout periods for brimonidine 0.2 % and latanoprost 0.005%*, Am J Opthalmol Jun. 2001;131(6):798-799.
Takano, et al, 1993, Mol.Bio. Cell 4:358A.
Tracey, M.A., et al. *Factors affectivethe degradation rate of poly(lactide-co-glycolide)microspheres in vivo and in vitro*, Biomaterial 20:1057-1062 (1999).
USP 23; NF 18 (1995) pp. 1790-1798.
The Wall Street Transcript (TWCT); 7 pages, published by the Wall Street Transcript Corp.; published Dec. 2000.
Wingate, R.J., et al., Intravitreal Triamcinolone and Elevated Intraocular Pressure, Australian and New Zealand J. of Opthalmology, 27(6):431-2, Dec. 1999, 2 pgs.
Xu et al, "Permeability and Diffusion in Vitreous Humor: Implications for Drug Delivery", Pharmceutical Research, 2000; 17(6): pp. 664-669.

Zhou, T, et al. (1998). *Development of a multiple-drug delivery implant for intraocular management of proliferative vitreoretinopathy*, Journal of Controlled Release 55: 281-295.
U.S. Appl. No. 60/587,092, filed Jul. 2004.
U.S. Appl. No. 07/357,394, filed May 1989.
U.S. Appl. No. 07/386,835, filed Jul. 1989.
U.S. Appl. No. 10/820,562, filed Apr. 2004.
U.S. Appl. No. 10/837,357, filed Apr. 30, 2004.
U.S. Appl. No. 11/180,752, filed Jul. 11, 2005.
U.S. Appl. No. 13/236,432, filed Sep. 19, 2011.
Aguilar, H.E., et al. "Vancomycin Levels After Intravitreal Injection," *Retina*, 1995; 15:428-432.
Ahmad, M., et al. "Ortho Ester Hydrolysis: Direct Evidence for a Three-Stage Reaction Mechanism," *Journal of American Chemistry*, 1979; 101(10):2669-2677.
Ahmed, I., et al. "Macular disorders: cystoid macular edema," *Ophthalmology*, Yanoff, M., Duker, J.S., eds. London: Mosby, 1999; 34.1-34.6.
Akduman, L., et al. "The early treatment diabetic retinopathy study," *Clinical trials in ophthalmology: a summary and practice guide*, Kertes, P.S., Conway, M.D., eds. Baltimore: Williams & Wilkins, 1998; 15-35.
Algvere, P.V., et al. "Transplantation of RPE in Age-Related Macular Degeneration: Observations in Disciform Lesions and Dry RPE Atrophy," *Gratfe's Archives of Clinical Exerimental Ophthalmology*, 1997; 235(3):149-158.
Anderson, L.C., et al. "An Injectable Substained Release Fertility Control System," *Contraception*, 1976; 13:375-384.
Aradreau, K., et al. "Induction of apoptosis by dexamethasone in the B cell lineage," *Immunopharmacology*, Jul. 1998; 40(1):67-76.
Antcliff, R, et al. "The pathogenesis of edema in diabetic maculopathy," *Seminars in Ophthalmology*, 1999; 14:223-232.
Apel, A., et al. "A Subconjunctival Degradable Implant for Cyclosporine Delivery in Corneal Transplant Therapy," *Current Eye Research*, 1995; 14(8):659-667.
Arnie, M. and Maurice, D.M. "The Loss of Fluorescein, Fluorescein Glucuronide and Fluorescein Isothiocyanate Dextran From the Vitreous by the anterior and Retinal Pathways," *Experimental Eye Research*, 1991; 52:27-39.
Baker, R. "Monolithic Devices," *Controlled Release of Biologically Active Agents*, New York: John Wiley & Sons, 1987; 50-75.
Barnas, U., et al. "Parameters Associated with Chronic Renal Transplant Failure," *Nephrology Dialysis Transplantation*, 1997; 12(Suppl 2):82-85.
Bauza, M., et al. "Pharmacokinetics of Intravitreal Carbenicillin, Cefazolin, and Gentamicin in Rhesus Monkeys," *Investigative Ophthalmology & Visual Science*, 1983; 24:1602-1606.
Beck, R.W., et al. "The Effect of Corticosteroids for Acute Optic Neuritis on the Subsequent Development of Multiple Sclerosis," *New England Journal of Medicine*, 1993; 329(24):1764-1769.
Beck, R.W., et al. "A randomized, controlled trial of corticosteroids in the treatment of acute optic neuritis," *New England Journal of Medicine*, Feb. 27, 1992; 326(9):634-5.
Bennett, W.M. and Barry, J.M. "Failure of Dexamethasone to Provide Adequate Chronic Immunosuppression for Renal Transplantation," *Transplantation*, 1979; 27(3):218-219.
Ben-Nun, J., et at "Pharmacokinetics of Intravitreal Injection," *Investigative Ophthalmology & Visual Science* 1989; 30(6):1055-1061.
Bigar, F. and C.P. Herbort. "Corneal Transplantation," *Current Opinion in Ophthalmology*, 1992; 441:473-481.
Bingaman, D.P., et al. "Inhibition of preretinal neovascularization in pigs by intravitreal triamcinolone acetonide," *Investigative Ophthalmology and Visual Science*, 1995; 36(4):S401, abstract 1867.
Bito, L.Z. "Prostaglandins and Related Compounds as Potential Ocular Therapeutic Agents," *Biological Protection with Prostaglandins*, vol. 1, Cohen, M.M. ed., Boca Raton: CRC Press Inc., 1985; 31-252.
Bito, L.Z. "Prostaglandins, Other Eicosanoids, and their Derivatives as Potential Antiglaucoma Agents," *Glaucoma: Applied Pharmacology in Medical Treatment*, Drance, S.M. and Neufled, A.H. Eds., New York: Grune & Stratton, 1984; 477-505.
Bito, L.Z. "Prostaglandins: Old Concepts and New Perspectives," *Archives of Ophthalmology*, 1987; 105:1036-1039.

(56) References Cited

OTHER PUBLICATIONS

Brubaker, R.F. "Mechanism of Action of Bimatoprost (Lumigan™)," *Survey of Ophthalmology*, 2001; 45(Suppl 4):S347-S351.

Budavari, S., et al. eds. *The Merck Index*, 12$^{th}$ ed. Rahway, NJ: Merck and Co., 1996; Table of Contents only.

Bundgaard, H. and Moss, J. "Prodrugs of Peptides IV: Bioreversible Derivatization of the Pyroglutamyl Group by N-Acylation and N-Aminomethylation to Effect Protection against Pyroglutamyl Aminopeptidease," *Journal of Pharmaceutical Sciences*, 1989; 78(2):122-126.

Burden, M.A. and P. McDonnell. "A Survey of Corneal Graft Practice in the United Kingdom," *Eye*, 1995; 9(Suppl):6-12.

Checko, D.M., et al. "Survival and Differentiation of Cultured Retinal Progenitors Transplanted in the Subretinal Space of the Rat," *Biochemical and Biophysical Research Communications*, 2000; 268(3):842-846.

Challa, J.K., et al. "Exudative Macular Degeneration and Intravitreal Triamcinolone: 18 month follow up," *Australian and New Zealand Journal of Ophthalmology*, 1998; 26:277-281.

Chang, David, et al. "Phase II results of an intraocular steroid delivery system for cataract surgery,7" *Ophthalmology*, Jun. 1996; 106(6):1172-1177.

Chang, M., et al. "Basic Science and Clinical Aspects of Wound Healing in Glaucoma Filtering Surgery," *Journal of Ocular Pharmacology and Therapeutics*, 1998; 14(1):75-95.

Charles, J., et al. "Use of Bioerodible Polymers Impregnated with Mitomycin in Glaucoma Filtration Surgery in Rabbits," *Ophthalmology*, Apr. 1991; 98(4):503-508.

Chen, J., et al. "Lumigan®: A Novel Drug for Glaucoma Therapy," *Optometry in Practice*, 2002; 3:95-102.

Clarkson, J.G. "Central retinal vein occlusion," *Retina*, 3$^{rd}$ ed. Ryan, S., Schachat, A.P., eds. St. Louis, MO: CV Mosby; 2001; 1368-1375.

Coleman, A.L., et al. "A 3-Month Randomized Controlled Trial of Bimatoprost (Lumigan) Versus Combined Timolol and Dorzokunide (Cosopt) in Patients with Glaucoma or Ocular Hypertension," *Ophthalmology*, 2003; 110(12):2362-2368.

Cuff, G. and Raoul, F. "A Preliminary Evaluation of Injection Molding as a Technology to Produce Tablets," *Pharmaceutical Technology*, 1998; 96-106.

Davis, P.A., et al. "Intraocular Implant for Controlled 5-Fluorouracil Release," *Proceedings of the 19th International Symposium of Controlled Release Bioactive Materials*, 1992; 19:339-340.

De Jong, S.J., et al. "New insights into the hydrolytic degradation of poly(lactic acid): participation of the alcohol terminus," *Polymer*, 2001; 42:2795-2802.

Di Colo, G. "Controlled Drug Release From Implantable Matrices Based on Hydrophobic Polymers," *Biomaterials*, 1992; 13(12):850-856.

Dick, J., et al. "Macular edema," *Retina*, 3$^{rd}$ ed. Ryan, S., Schachat, A.P., eds. St. Louis, MO: CV Mosby; 2001; 967-979.

Dinning, W.J. "Intermediate Uveitis: history, terminology definition pars planitis: systemic disease associations," *Developments in Ophthalmology: Intermediate Uveitis*, W.R.F. Böke, et al. eds. Basel: Karger, 1992; 3-8.

Druilhe, A., et al. "Glucocorticoid-induced apoptosis in human eosinophils: mechanisms of action," *Apoptosis*, Oct. 2003; 8(5):481-95.

*Encyclopedia of Polymer Science and Technology*, vol. 3. New York: Interscience Publishers, Inc., 2003; Table of Contents only.

Enzmann, V., et al. "Immunological Problems of Transplantation into the Subretinal Space," *Acta Anatomica*, 1998 162(2-3):178-183.

Fatt, I. "Flow and Diffusion in the Vitreous Body of the Eye," *Bulletin of Mathematical Biology*, 1975; 37:85-90.

Fekrat, S. and Finkelstein, D. "The Central Vein Occlusion Study," *Clinical trials in ophthalmology; a summary and practice guide*, Kertes, P.S., Conway, M.D., eds. Baltimore, MD: Williams & Wilkins, 1998; 129-143.

Frank, R.N. "Etiologic mechanisms in diabetic retinopathy," *Retina*, 3$^{rd}$ed. Ryan, S., Schachat A.P., eds. St. Louis, MO: CV Mosby; 2001; 1259-1294.

Friedrich, S., et al. "Finite Element Modeling of Drug Distribution in the Vitreous Humor of the Rabbit Eye," *Annals of Biomedical Engineering*, 1997; 25:303-314.

Gennaro, A.R. ed. *Remington: The Science and Practice of Pharmacy*, 19$^{th}$ Ed. Easton, PA: Mack Publishing Company, 1995; Table of Contents only, xv-xvi.

Gilman, A.G., et al. eds. *Goodman and Gilman's: The Pharmacological Basis of Therapeutics*. 8$^{th}$ Ed. New York: Pergamon Press, 1990; Table of Contents only, xi-xvi.

Goldberg, Ivan, "Drugs for glaucoma," *Australian Prescriber*, 2002; 25(6)142-146.

Goodman, L.S. and A. Gilman eds. *The Pharmacological Basis of Therapeutics*, 9$^{th}$ Ed. New York: McGraw-Hill, 1996; Table of Contents only, v-xii.

Gould, L., et al. "Fifty:fifty Poly (DL Glycolic Acid-Lactic Acid) Copolymer as a Drug Delivery System for 5-Fluorouracil: A Histopathological Evaluation," *Canadian Journal of Ophthalmology*, 1994; 29(4):168-171.

Greenfield, R.S., et al. "Evaluation in Vitro of Adriamycin Immunoconjugtes Synthesized Using an Acid-sensitive Hydrazone Linker," *Cancer Research*, 1990; 50:6600-6607.

Guan, D., et al. "Therapeutic Window of Cyclosporine in Chinese Recipients of Renal Transplantation," *Transplantation Proceedings*, 1995; 27(1):850-851.

Hari, P. and Srivastava, R.N. "Pulse Corticosteroid Therapy with Methylpreprednisolone or Dexamethasone," *Indian Journal of Pediatrics*, 1998; 65(3):557-560.

Haynes, Robert C. Jr. "Adrenocorticotropic Hormone; Adrenocortical Steroids and their Synthetic Analogs; Inhibitors of the Synthesis and Actions of Adrenocortical Hormones," *Goodman and Gilman's; The pharmacological Basis of Therapeutics*, 8th Ed. New York: Pergamon Press, 1990; 1431-1462.

Hardt, S.S. "Posterior Drainage of the Intraocular Fluid From the Vitreous," *Experimental Eye Research*,1996; 5:123-144.

Heller, J. "Bioerodible Hydrogels," *Hydrogels in Medicine and Pharmacy, vol. 3; Properties and Applications*, N.A. ed. Boca Raton: CRC Press, 1987; 138-149.

Heller, J. "Poly (Ortho Esters)," *BIopolymers I*, Pappas, N.A. and R.S. Langer eds. New York: Springer-Verlag, 1993; 41-92.

Heller, J., at al. "Poly(ortho ester) Biodegradable Polymer Systems," *Methods in Enzymology*, Widder, K.J. and R. Green eds. Orlando: Academic Press, Inc., 1985; 422-436.

Hirano, T. "Clinical Significance of Glucocorticoid Pharmacodynamics Assessed by Antilymphocyte Action in Kidney Transplantation," *Transplantation*, 1994; 57(9):1341-1348.

Höckel, M., et al. "Prevention of Peritoneal Adhesions in the Rat With Sustained Intraperitoneal Dexamethasone Delivered by a Novel Therapeutic System," *Annales Chirurgiae et Gynaecologiae*, 1987; 76(6):306-313.

Inoue, M., et al. "Vitreous Concentrations of Triamcinolone Acetonide in Human Eyes After Intravitreal or Subtenon Injection," *American Journal of Ophthalmology*, 2004; 138(6):1046-8.

Jackanicz, T., et al. "Polyactic Acid as a Biogradable Carrier for Contraceptive Steroids" *Contraception*, 1973; 8(3):227-234.

Jaffe, G.J., et al. "Safety and Pharmacokinetics of an Intraocular Fluocinolone Acetonide Sustained Delivery Device," *Investigative Ophthalmology & Visual Science*, 2000; 41(11):3569-3575.

Jaffe, G.J., et al. "Safety, Efficacy, and Pharmacokinetics of an Intravitreal Fluocinolone Sustained Drug Delivered System," *Investigative Ophthalmology & Visual Science*, 1999; 40(4):S988, abstract 5195.

Jampel, H., et al. "Glaucoma Filtration Surgery in Monkeys Using 5-Fluorouridine in Polyanhydride Disks," *Archives of Ophthalmology*, Mar. 1990; 108(3):430-435.

Jay, W.M., et al. "Intravitreal Ceftazidime in a Rabbit Model: Dose- and Tune-Dependent Toxicity and Pharmacokinetic Analysis," *Journal of Ocular Pharmacology*, 1987; 3(3):257-262.

Jennings, T., et al. "Posterior sub-Tenon's injections of corticosteroids in uveitis patients with cystoid macular edema," *Japanese Journal of Ophthalmology*, 1988; 32(4):385-391.

Jeong, J.H., et al. "Novel Intracellular Delivery System of Antisense Oligonucleotide by Self-Assembled Hybrid Micelles Composed of

(56) References Cited

OTHER PUBLICATIONS

DNA/PEG Conjugate and Cationic Fusogenic Peptide," *Bioconjugate Chemistry*, 2003; 14:473-479.
Johnson, F. and Maurice, D. "A Simple Method of Measuring Aqueous Humor Flow With Intravitreal Fiuoresceinated Dextrans," *Experimental Eye Research*, 1984; 39:791-805.
Kane, A., et al. "Intravitreal Injection of Gentamicin in Rabbits," *Investigative Ophthalmology & Visual Science*, 1981; 20(5):593-597.
Kang, S.W., et al. "Macular grid photocoagulation after intravitreal triamcinolone acetonide for diffuse diabetic macular edema," *Archives of Ophthalmology*, May 2006; 124(5):653-8.
Kher, V., et al. "Low-Dose Dexamethasone13 An Alternative Therapy for Acute Renal Allograft Rejection," *Transplantation Proceedings*, 1992; 24(5):1725.
Kimaura, H. and Ogura, Y. "Biodegradable Polymers for Ocular Drug Delivery," *Ophthalmologica*, 2001; 215:143-155.
Kochinke, F. and Wong, V.G. "Biogradable Drug Delivery System for Uveitis Treatment, Oculex Pharmaceuticals, Inc.," Slide Presentation, 1996; total pp. 20.
Kralinger, M.T., et al. "Slow Release of Acetysalicyclic Acid by Intravitreal Silicone Oil," *Retina: The Journal of Retinal and Vitreous Diseases*, 2001; 21(5):513-520.
Kunou, Noriyuki, et at "Biodegradable scleral implant for controlled intraocular delivery of betamethasone phosphate," *Journal of Biomedical Materials Research*, 2000; 51(4):635-641.
Kwak, H.W. and D'Amico, D.J. "Evaluation of the Retinal Toxicity and Pharmacokinetics of Dexamethasone After Intravitreal Injection," Archives of Ophthalmology, 1992; 110:259-266.
Laurent, U.B.G. and Fraser, J.R.E. "Turnover of Hyaluronate in the Aqueous Humor and Vitreous Body of the Rabbi" *Experimental Eye Research*, 1983; 36:493-504.
Lee, D., et al. "Complications of Subconjunctival 5-Fluorouracil Following Glaucoma Filtering Surgery," *Ophthalmic Surgery*, Mar. 1987; 18(3):187-190.
Lee, D., et al. "Glaucoma Filtration Surgery in Rabbits Using Bioerodible Polymers and 5-Fluorouracil," *Ophthalmology*, Dec. 1987; 94(12):1523-1530.
Lee, D., et al. "The Use of Bioerodible Polymers and 5-Fluorouracil in Glaucoma Filtration Surgery," *Investigative Ophthalmology & Visual Science*, Nov. 1988; 29(11): 1692-1697.
Lee, K.Y. and Wong, V.G. "Dexamethasone Posterior Segment Drug Delivery System for Treatment of Severe Uveitis," *American Uveitis Sociey*, 1999; Abstract.
Leopold, I.H. "Nonsteroidal and steroidal anti-inflammatory agents," *Surgical pharmacology of the Eye*, Sears, M., Tarkkanen, A., eds. New York: Raven Press, 1985; 83-133.
Mathebula, S.D. "A Review of Pharmacological Therapy for Glaucoma," *The South African Optometrist*, Sep. 2005; 64(3):89-96.
Maurice, D.M. "The Exchange of Sodium Between the Vitreous Body and the Blood and Aqueous Humour," *Journal of Physiology*, 1957; 137:110-125.
Maurice, D.M. "Flow of Water Between Aqueous and Vitreous Compartments in the Rabbit Eye," *American Journal of Physiology*, 1987; 252 (1):F104-F108.
Maurice, D.M. and Mishima, S. "Ocular Pharmacokinetics," *Pharmacology of the Eye*, M.L. Sears ed. New York: Springer-Verlag, 1984; 19-116.
Meadows, D.L., et al. "Ocular Drug Delivery with Subconjunctival Implants," *Proceedings of the International Symposium on Controlled Release of Bioactive Materials*, Controlled Release Society, Inc., 1994; 21:593-594.
Migita, K., et al. "Apoptosis Induction in Human Peripheral Blood T Lymphocytes by High-Dose Steroid Therapy", *Transplantation*, 1997; 63(4):583-587.
Miller, R., et al. "Degradation Rates of Oral Resorbable Implants (Polylactates and Polyglycolates): Rate Modification with Changes in PLA/PGA Copolymer Ratios," *Journal of Biomedical Materials Research*, 1977; 11(5):711-719.

Mittel, R., et al. "Treatment of Acute Rejection in Live Related Renal Allograft Recipients: A Comparison of Three Different Protocols," *Nephron*, 1977; 77(2):186-189.
Morita, Y., et al. "Polymer Blend Implant for Ocular Delivery of Fluorometholone," *Biological & Pharmaceutical Bulletin*, 1998; 21(1):72-75.
Moseley, H., et al. "Routes of Clearance of Radioactive Water From the Rabbit Vitreous," *British Journal of Ophthalmology*, 1984; 68:145-151.
Nauck, M., et al. "Corticosteroids inhibit the expression of the vascular endothelial growth factor gene in human vascular smooth muscle cells," *European Journal of Pharmacology*, 1998; 341:309-315.
Nauck, M., et al. "Induction of vascular endothelial growth factor by platelet-activating factor and platelet-derived growth factor is dowmegulatal by corticosteroids," *American Journal of Respiratory Cell and Molecular Biology*, 1997; 16:398-406.
Nilsson, S.F.E., et al. "PGF2 Increases Uveoscleral Outflow," *Investigative Ophthalmology & Visual Science*, 1987; 28(3):284, abstract 9.
Ogden, T.E., et al eds. *Retina—Basic Science and Inherited Retinal Disease* vol. 1, St. Louis: CV Mosbyz, 1994; Table of Contents, xxiii-xxix.
Ohtori, A. and Tojo, K. "In vivo/in Vitro Correlation of Intravitreal Delivery of Drugs With the Help of Computer Simulation," *Biological & Pharmaceutical Bulletin*, 1994; 17(2)283-290.
Oplinger, N.L., et al. "A Comparison of Corneal Autografts With Homografts," *Ophthalmic Surgery and Lases*, 1998; 29(4):305-308.
Orth, D. "The branch vein occlusion study," *Clinical trials in ophthalmology: A summary and practice guide*, Kertes, P. and Conway, M, eds., Baltimore, MD: Williams & Wilkins, 1998: 113-127.
Park., T.G., et al. "A new preparation method for protein loaded poly (D,L-lactic-co-glycolic acid) microspheres and protein release mechanism study," *Journal of Controlled Release*, 1998; 55: 181-191.
Patel, N.P., et al. "Indications for and Outcomes of Repeat Penetrating Keratoplasty, 1989-1995," *Ophthalmology*, 2000; 107(4):719-724.
Pearson, P.A., et al. "Clearance and Distribution of Ciprofloxacin After Intravitreal Injection," *Retina*, 1993; 13:326-330.
Pe'er, J., et al. "Vascular endothelial growth factor by platelet-activating factor upregulation in human central retinal vein occlusion," *Ophthalmology*, 1998; 105:412-416.
Peyman, G.A. and Herbst, R. "Bacterial endophthalmitis," *Archives of Ophthalmology*, 1974; 91(5):416-418.
Peyman, G.A., et al. "A Technique for Retinal Pigment Epithelium Transplantation for Age-Related Macular Degeneration Secondary to Extensive Subfoveal Scarring," *Ophthalmic Surgery*, 1991; 22(2):102-108.
Pinar, V. "Intermediate Uveitis," *Massachusetts Eye & Ear Infirmary Immunology Service*, Boston.
Rahil, J., at al. "Reactivity and Mechanism of Hydrolysis of Phosphonamides," *Journal of the American Chemical Society*, 1981; 103:1723-1734.
Rao, K.V., et al. "Successful Renal Transplantation in a Patient With Anaphylactic Reaction to Solu-Medrol (Methylprednisolone Sodium Succinate)," *American Journal of Medicine*, 1982;72(1):161-163.
Riordan-Eva, P., et al. "Orbital floor steroid injections in the treatment of uveitis," *Eye*, 1994; 8(1):66-69.
Robin, Jeffrey B., et al. "The Histopathology of Corneal Neovascularization," *Archives of Ophthalmology*, 1985; 103(2):284-287.
Rof W.J. and Scott, J.R. eds. *Handbook of Common Polymers*, Cleveland: CRC Press, 1971; Table of Contents.
Rootman, D.S., et al "Toxicity and Pharmacokinetics of Intravitreally Injection Ciprofloxacin in Rabbit Eyes," *Canadian Journal of Ophthalmology*, 1992; 27(6):277-282.
Sasaki, H., et al "Drug Absorption Behavior After Periocular Injections," *Biological & Pharmaceutical Bulletin*, 1999; 22(9):956-960.
Schimmer B.P. and Parker K.L. "Adrenocorticotropic hormone; Adrenocortical Steroids and their Synthetic Analogs; Inhibitors of the Synthesis and Actions of Adrenocortical Hormones," *The Phar-*

(56) References Cited

OTHER PUBLICATIONS macological Basis of Therapeutics 10ed., Hardman, J.G. and Limbard, L.L. eds, New York: McGraw-Hill, 2001; 1649-1677.

Schindler, R.H., et al. "The Clearance of Intravitreal Triamcinolone Acetonide," *American Journal of Ophthalmology*, 1982; 93(4):415-417.

Scholes, G.N., et al. "Clearance of Triamcinolone From Vitreous," *Archives of Ophthalmology*, 1985; 103(10):1567-1569.

Scott, J.R. and W.J. Roff eds."Permeability," *Handbook of Common Polymers*, Cleveland: CRC Press, 1971; 554-558.

Shields, Bruce M. "Glaucoma Filtering Procedures," *A Study for Glaucoma*, Baltimore: Williams & Wilkins, 1982; 453-476.

Siebold, et al. *Prodrug*, 1989; 5:3.

Smith, T., et al. "Sustained-release subconjunctival 5-Fluorouracil," *Ophthalmic Surgery and Lasers*, Sep. 1996; 27(9):763-767.

Starr, M.S. "Further Studies on the Effect of Prostaglandin on Intraocular Pressure in the Rabbit," *Experimental Eye Research*, 1971; 11(2):170-177.

Taba, K.E., et al. "Intravitreal sustained release fluocinolone implant inhibits experimental choroidal neovascularization," *Investigative Ophthalmology & Visual Science*, Mar. 1999; 40(4):S172, abstract 920.

Tan, D.T.H., et al. "Randomized Clinical Trial of a New Dexamethasone Delivery System (Surodex) for Treating of Post-Cataract Surgery Inflammation," *Ophthalmology*, 1999; 106(2):223-231.

Tennant, J.L. "Cystoid maculopathy," *Current concepts in cataract surgery: selected proceedings of the fifth biennial cataract surgical congress*, Emery, J.M. ed. St. Louis: CV Mosby, 1978; 360-362.

Theng, J.T.S., et al. "Pharmacokinetic and Toxicity Study of an Intraocular Cyclosporine DDS in the Anterior Segment of Rabbit Eyes," *Investigative Ophthalmology & Visual Science*, Nov. 2003; 44(11):4895-4899.

Tsubota, K. "Ocular Surface Management in Corneal Transplantation, A Review," *Japanese Journal of Ophthalmology*, 1999; 43(6):502-508.

Turcotte, J.G., et al. "Rejection Crises in Human Renal Transplant Recipients: Control with High Dose Methylprednisolone Therapy," *Archives of Surgery*, 1972; 105(1):230-236.

*The United States Pharmacopeia, The National Formulary*, "USP 24/NF 19," 2000; 1941-1951.

Watson, P., et al. "A Six-month, Randomized, Double-masked Study Comparing Latanoprost with Timolol in Open-angle Glaucoma and Ocular Hypertension," *Ophthalmology*, 1996; 103(1):126-137.

Weisbecker, C.A., et al., eds. *Physician' Desk Reference for Ophthalmology 27th ed.*, Montvale, NJ: Medical Economics Company, 1998; 7-8, 278-279.

Woodward, D.F., et al. "AGN 192024 (Lumigan®): A Synthetic Prostamide Analog that Lowers Primate Intraocular Pressure by Virtue of Its Inherent Pharmacological Activity," *Investigative Ophthalmology & Visual Science*, 2002; 43, abstract 4110.

Woodward, D.F., et al. "The Pharmacology of Bimatoprost (Lumigan™)," *Survey of Ophthalmology*, 2001; 45(Suppl 4):S337-S345.

\* cited by examiner

Vitreous Humor Concentrations of Dexamethasone in Treated Eye: Comparison of all Dose Levels and Dosage Forms Percent of Dexamethasone Released from DEX PS DDS over Time for all Dose Levels and Dosage Forms Vitreous Humor Concentrations of Dexamethasone in Treated Eye:
Comparison of all Dose Levels and Dosage Forms Percent of Dexamethasone Released from DEX PS DDS Over Time for
all Dose Levels and Dosage Forms

METHODS FOR TREATING RETINOPATHY WITH EXTENDED THERAPEUTIC EFFECT

CROSS REFERENCE

The present application is a continuation of U.S. patent application Ser. No. 14/306,363, filed on Jun. 17, 2014, which is a continuation of U.S. patent application Ser. No. 13/946,294, filed on Jul. 19, 2013, which is a continuation of U.S. patent application Ser. No. 13/604,809, filed on Sep. 6, 2012, which is a continuation of U.S. patent application Ser. No. 11/292,544, filed Dec. 2, 2005, which is a continuation in part of U.S. patent application Ser. No. 10/837,357, filed Apr. 30, 2004, the entire contents of all of the preceding applications are hereby incorporated by reference.

BACKGROUND

This invention relates to methods for extended treatment of an ocular condition. In particular the present invention releases to methods for extended treatment of an ocular condition with an intraocular implant.

An ocular condition can include an inflammatory, neoplastic, infectious, vascular, neovascular and/or degenerative disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region, location or site (hereafter an ocular site), such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site. A posterior ocular condition is a disease, ailment or condition which primarily affects or involves a posterior ocular site such as choroid or sclera (in a position posterior to a plane through the posterior wall of the lens capsule), vitreous, vitreous chamber, retina, optic nerve (including the optic disc), and blood vessels and nerves which vascularize or innervate a posterior ocular site.

Thus, a posterior ocular condition can include a disease, ailment or condition, such as for example, macular degeneration (such as non-exudative age related macular degeneration and exudative age related macular degeneration); macular hole; light, radiation or thermal damage to a posterior ocular tissue; choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or retinal ganglion cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; hyperopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

The present invention is directed to a method for providing an extended treatment of an ocular condition, such as an anterior ocular condition or a posterior ocular condition or to an ocular condition which can be characterized as both an anterior ocular condition and a posterior ocular condition.

Therapeutic compounds useful for the treatment of an ocular condition can include cytokines and active agents with, for example, an anti-neoplastic (i.e. anti-cancer), anti-angiogenesis, kinase inhibition, anticholinergic, anti-adrenergic and/or anti-inflammatory activity.

Macular degeneration, such as age related macular degeneration ("AMD") is a leading cause of irreversible vision loss in elderly populations. It is estimated that thirteen million Americans have evidence of macular degeneration. Macular degeneration results in a break down or injury to the macula, the central part of the retina responsible for the sharp, direct vision needed to read or drive. Central vision is especially or selectively affected. Macular degeneration is diagnosed as either dry or wet (exudative). The dry form of macular degeneration is more common than the wet form of macular degeneration, with about 90% of AMD patients being diagnosed with dry AMD. The wet form of the disease usually leads to more rapid and more serious vision loss. Macular degeneration can produce a slow or sudden painless loss of vision. The cause of macular degeneration is not clear. The dry form of AMD may result in thinning of macular tissues, depositing of pigment in the macula, or a combination of the two processes. With wet AMD, new blood vessels grow within and beneath the retina and leak blood and fluid. This leakage causes injury to retinal cells and creates blind spots in central vision.

Macular edema (ME) can result in a swelling or thickening of the macular and appears to be a nonspecific response of the retina to a variety of insults. Thus, ME is associated with a number of diseases, including anterior or posterior uveitis, retinal vascular abnormalities (diabetic retinopathy and retinal venous occlusive disease), as a sequela of cataract surgery (Irvine-Gass Syndrome), macular degeneration, vitreomacular traction syndrome, inherited or acquired retinal degeneration, eye inflammation, idiopathic central serous chorioretinopathy, pars planitis, retinitis pigmentosa, radiation retinopathy, posterior vitreous detachment, epiretinal membrane formation, idiopathic juxtafoveal retinal telangiectasia, following Nd:YAG capsulotomy or iridotomy. Some patients with ME may have a history of use of topical epinephrine or prostaglandin analogs for glaucoma. Macular edema involves the development of microangiopathy, characterized by abnormal retinal vessel permeability and capillary leakage into the adjacent retinal tissues. The macula becomes thickened due to accumulation of fluid which leaks out of weak blood vessel walls due to a breakdown of the inner blood-retinal barrier at the level of the capillary endothelium, often resulting in significant disturbances in visual acuity. The blood and fluid leaks out of the weak vessel walls into a very small area of the macula which is rich in cones, the photoreceptors that detect color and from which daytime vision depends. Blurring then occurs in the middle or just to the side of the central visual field. Visual loss can progress over a period of years. Symptoms of ME include blurred central vision, distorted vision, vision tinted pink and light sensitivity.

In some cases macular edema can resolves spontaneously or with show remission after a short-term treatment. However, in cases of persistent macular edema (PME), visual loss continues to be a significant therapeutic challenge. Therapies for macular edema utilize a stepwise approach including surgical and medical methods. A first line of treatment for certain types of ME can be anti-inflammatory drops topically applied. Currently there are no approved therapies for the treatment of PME. Macular edema that has failed to respond to drug therapy and laser photocoagulation represents a significant unmet medical need.

Drug therapy for macular edema can include topical, periocular, subconjunctival/intravitreal, or systemic corticosteroids; topical and systemic nonsteroidal anti-inflammatory agents (NSAIDs); and/or immunosuppressants. Nonetheless, with variable incidence, macular edema can persist regardless of treatment or causation resulting in severe vision loss. Liquid, intravitreal triamcinolone acetonide (available from Bristol Myers Squibb under the tradename Kenalog-40®) injection has been used to treat ocular inflammation and macula edema. Kenalog-40® is a suspension triamcinolone acetonide (40 mg/mL) formulated with sodium chloride for isotonicity, 0.9% (w/v) benzyl alcohol as preservative, 0.75% carboxymethylcellulose sodium, and 0.04%, polysorbate 80. It is approved for intramuscular depot delivery for the treatment of inflammation and has been used intravitreally to treat ocular inflammation as well as macular edema due to numerous causes. Unfortunately, side-effects including elevated intraocular pressure, cataract, endophthalmitis (such as infectious endophthalmitis and sterile endophthalmitis), retinal toxicity and crystalline retinal deposits have been reported from clinical use of intravitreal triamcinolone acetonide.

Surgical methods for the treatment of macular edema including laser photocoagulation have had mixed results. Focal/grid laser photocoagulation for the prevention of moderate visual loss has been shown to be efficacious in diabetic retinopathy and branch retinal vein occlusion patients, but not in central retinal vein occlusion patients. As a last resort, a vitrectomy is sometimes performed in patients who have persistent macular edema that has failed to respond to less invasive treatments.

Dexamethasone, a potent anti-inflammatory in the corticosteroid family, has been shown to suppress inflammation by inhibiting edema, fibrin deposition, capillary deposition and phagocytic migration of the inflammatory response. Corticosteroids prevent the release of prostaglandins which have been identified as one of the causative agents of cystoid macular edema. Additionally, corticosteroids including dexamethasone have also been shown to have potent anti-permeability activity by inhibiting the synthesis of VEGF. Despite known anti-inflammatory and anti-permeability properties, use of corticosteroid in the treatment of macular edema has been limited because of the inability to deliver and to maintain adequate quantities of the drugs at the macular without resultant toxicities.

Previously, dexamethasone use has yielded varying degrees of success in treating retinal disorders including macular edema largely due to the inability to deliver and maintain adequate quantities of the drug to the posterior segment (vitreous) without resultant toxicities. Topical administration of 1 drop (50 µl) of a 0.1% dexamethasone ophthalmic suspension, 4 times a day is equivalent to approximately 200 µg per day, however, only about 1% (2 µg per day) reaches the anterior segment, and only a fraction of that amount moves into the posterior segment (vitreous). Although intravitreal injections of dexamethasone have been used, the exposure of the drug is very temporal as the half-life of the drug within the eye is approximately 3 hours, Periocular and posterior sub-Tenon's injections of dexamethasone have been used, but with only short-term treatment effect.

Treatment with corticosteroids must be monitored closely due to potential toxicity and long-term side effects. Adverse reactions listed for conventional ophthalmic dexamethasone preparations include: glaucoma (with optic nerve damage, visual acuity and field defects), posterior subcapsular cataract formation, and secondary ocular infection from pathogens including herpes simplex. Systemic doses of dexamethasone can be as high as 9000 µg/kg/day, of which only a small portion reaches the posterior segment, and may be associated with additional hazardous side-effects including hypertension, hyperglycemia, increased susceptibility to infection, and peptic ulcers.

Although an efficient means of delivering a drug to the posterior segment is direct delivery into the vitreous body, the natural pharmacokinetics of the eye typically result in a short half-life unless the drug can be delivered using a formulation capable of providing sustained release. By delivering a drug intravitreally, the blood-eye barrier is circumvented and intraocular therapeutic levels can be achieved without the risk of systemic toxicity.

An anti-inflammatory (i.e. immunosuppressive) agent can be used for the treatment of an ocular condition which involves inflammation, such as an uveitis or macula edema. Thus, topical or oral glucocorticoids have been used to treat uveitis. A major problem with topical and oral drug administration is the inability of the drug to achieve an adequate (i.e. therapeutic) intraocular concentration. See e.g. Bloch-Michel E. (1992). *Opening address: intermediate uveitis*, In Intermediate Uveitis, *Dev. Ophthalmol*, W. R. F. Böke et al. editors., Basel: Karger, 23:1-2; Pinar, V., et al. (1997). *Intraocular inflammation and uveitis*" In Basic and Clinical Science Course. Section 9 (1997-1998) San Francisco: American Academy of Ophthalmology, pp. 57-80, 102-103, 152-156; Böke, W. (1992). *Clinical picture of intermediate uveitis*, In Intermediate Uveitis, Dev. Ophthalmol. W. R. F. Böke et al. editors., Basel: Karger, 23:20-7; and Cheng C-K et al. (1995). *Intravitreal sustained-release dexamethasone device in the treatment of experimental uveitis*, Invest. Ophthalmol. Vis. Sci. 36:442-53.

Systemic glucocorticoid administration can be used alone or in addition to topical glucocorticoids for the treatment of uveitis. However, prolonged exposure to high plasma concentrations (administration of prednisone 1 mg/kg/day for 2-3 weeks) of steroid is often necessary so that therapeutic levels can be achieved in the eye.

Unfortunately, these high drug plasma levels commonly lead to systemic side effects such as hypertension, hyperglycemia, increased susceptibility to infection, peptic ulcers, psychosis, and other complications. Cheng C-K et al. (1995). *Intravitreal sustained-release dexamethasone device in the treatment of experimental uveitis*, Invest. Ophthalmol. Vis. Sci. 36:442-53; Schwartz, B. (1966). The response of ocular pressure to corticosteroids, Ophthalmol. Clin. North Am. 6:929-89; Skalka, H. W. et al. (1980). *Effect of corticosteroids on cataract formation*, Arch Ophthalmol 98:1773-7; and Renfro, L. et al. (1992). *Ocular effects of topical and systemic steroids*, Dermatologic Clinics 10:505-12.

Additionally, delivery to the eye of a therapeutic amount of an active agent can be difficult, if not impossible, for drugs with short plasma half-lives since the exposure of the drug to intraocular tissues is limited. Therefore, a more efficient way of delivering a drug to treat a posterior ocular condition is to place the drug directly in the eye, such as directly into the vitreous. Maurice, D. M. (1983). *Micropharmaceutics of the eye*, Ocular Inflammation Ther. 1:97-102; Lee, V. H. L. et al. (1989). *Drug delivery to the posterior segment*" Chapter 25 In Retina. T. E. Ogden and A. P. Schachat eds., St. Louis: C V Mosby, Vol. 1, pp. 483-98; and Olsen, T. W. et al. (1995). *Human scleral permeability: effects of age, cryotherapy, transscleral diode laser, and surgical thinning*, Invest. Ophthalmol. Vis. Sci. 36:1893-1903.

Techniques such as intravitreal injection of a drug have shown promising results, but due to the short intraocular half-life of active agent, such as the glucocorticoid dexamethasone (approximately 3 hours), intravitreal injections must be frequently repeated to maintain a therapeutic drug level. In turn, this repetitive process increases the potential for side effects such as retinal detachment, endophthalmitis, and cataracts. Maurice, D. M. (1983). *Micropharmaceutics of the eye*, Ocular Inflammation Ther. 1:97-102; Olsen, T. W. et al. (1995). *Human scleral permeability: effects of age, cryotherapy, transscleral diode laser, and surgical thinning*, Invest. Ophthalmol. Vis. Sci. 36:1893-1903; and Kwak, H. W. and D'Amico, D. J. (1992). *Evaluation of the retinal toxicity and pharmacokinetics of dexamethasone after intravitreal injection*, Arch. Ophthalmol. 110:259-66.

Additionally, topical, systemic, and periocular glucocorticoid treatment must be monitored closely due to toxicity and the long-term side effects associated with chronic systemic drug exposure sequelae. Rao, N. A. et al. (1997). *Intraocular inflammation and uveitis*, In *Basic and Clinical Science Course*. Section 9 (1997-1998) San Francisco: American Academy of Ophthalmology, pp. 57-80, 102-103, 152-156; Schwartz, B. (1966). The response of ocular pressure to corticosteroids, *Ophthalmol Clin North Am* 6:929-89; Skalka, H. W. and Pichal, J. T. (1980). *Effect of corticosteroids on cataract formation*, Arch Ophthalmol 98:1773-7; Renfro, L and Snow, J. S. (1992). *Ocular effects of topical and systemic steroids*, Dermatologic Clinics 10:505-12; Bodor, N. et al. (1992). *A comparison of intraocular pressure elevating activity of loteprednol etabonate and dexamethasone in rabbits*, Current Eye Research 11:525-30.

U.S. Pat. No. 6,217,895 discusses a method of administering a corticosteroid to the posterior segment of the eye, but does not disclose a bioerodible implant.

U.S. Pat. No. 5,501,856 discloses controlled release pharmaceutical preparations for intraocular implants to be applied to the interior of the eye after a surgical operation for disorders in retina/vitreous body or for glaucoma.

U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. As shown by in vitro testing of the drug release kinetics, the 100-120 µg 50/50 PLGA/dexamethasone implant disclosed did not show appreciable drug release until the beginning of the fourth week, unless a release enhancer, such as HPMC was added to the formulation.

U.S. Pat. No. 5,824,072 discloses implants for introduction into a suprachoroidal space or an avascular region of the eye, and describes a methylcellulose (i.e. non-biodegradable) implant comprising dexamethasone. WO 9513765 discloses implants comprising active agents for introduction into a suprachoroidal or an avascular region of an eye for therapeutic purposes.

U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana. U.S. Pat. Nos. 5,443,505 and 5,766,242 disclose implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR). Zhou, T, et al. (1998). *Development of a multiple-drug delivery implant for intraocular management of proliferative vitreoretinopathy*, Journal of Controlled Release 55: 281-295.

U.S. Pat. No. 6,046,187 discusses methods and compositions for modulating local anesthetic by administering one or more glucocorticosteroid agents before, simultaneously with or after the administration of a local anesthetic at a site in a patient.

U.S. Pat. No. 3,986,510 discusses ocular inserts having one or more inner reservoirs of a drug formulation confined within a bioerodible drug release rate controlling material of a shape adapted for insertion and retention in the "sac of the eye," which is indicated as being bounded by the surfaces of the bulbar conjunctiva of the sclera of the eyeball and the palpebral conjunctiva of the eyelid, or for placement over the corneal section of the eye.

U.S. Pat. No. 6,369,116 discusses an implant with a release modifier inserted within a scleral flap.

EP 0 654256 discusses use of a scleral plug after surgery on a vitreous body, for plugging an incision.

U.S. Pat. No. 4,863,457 discusses the use of a bioerodible implant to prevent failure of glaucoma filtration surgery by positioning the implant either in the subconjunctival region between the conjunctival membrane overlying it and the sclera beneath it or within the sclera itself within a partial thickness sclera flap.

EP 488 401 discusses intraocular implants, made of certain polylactic acids, to be applied to the interior of the eye after a surgical operation for disorders of the retina/vitreous body or for glaucoma.

EP 430539 discusses use of a bioerodible implant which is inserted in the suprachoroid.

Significantly, it is known that PLGA co-polymer formulations of a bioerodible polymer comprising an active agent typically release the active agent with a characteristic sigmoidal release profile (as viewed as time vs percent of total active agent released), that is after a relatively long initial lag period (the first release phase) when little if any active agent is released, there is a high positive slope period when most of the active agent is released (the second release phase) followed by another near horizontal (third) release phase, when the drug release reaches a plateau.

Thus, there is a need for a extended therapeutic treatment of an ocular condition, such as posterior ocular condition. In particular, there is a need for treatment over an extended duration, for example, time periods extending up to 60 days, 90 days, 120 days, 6 months, 8 months, 12 months or more, after release of a therapeutic amount of a drug at an ocular site, such as the vitreous. Such extended treatment with an active agent can be advantageous to prevent recurrence of the inflammatory or other posterior ocular condition treated. It can also minimize the number of surgical interventions required by the patient over time to treat an ocular condition.

SUMMARY

The present invention meets these and other needs and provides for methods and implants which can provide an extended treatment of an ocular condition after release of a therapeutic amount of a drug from an implant placed in the vitreous and with maintenance of such a therapeutic effect for an extended period during which a therapeutic level or amount of the drug is not present is not detectable in the vitreous.

DEFINITIONS

The following terms as used herein have the following meanings:

"About" means approximately or nearly and in the context of a numerical value or range set forth herein means ±10% of the numerical value or range recited or claimed.

"Active agent" and "drug" are used interchangeably and refer to any substance used to treat an ocular condition.

"Anterior ocular condition" means a disease, ailment or condition which affects or which involves an anterior (i.e. front of the eye) ocular site, such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (behind the iris but in front of the posterior wall of the lens capsule), the lens or the lens capsule and blood vessels and nerve which vascularize or innervate an anterior ocular region or site.

"Bioerodible polymer" means a polymer which degrades in vivo, and wherein erosion of the polymer over time is required to release the active agent. The words "bioerodible" and "biodegradable" are synonymous and are used interchangeably herein.

"Extended" as in "extended therapeutic effect" means for a period of time greater than thirty days after release of all or all substantially all of an active agent in vivo from an intraocular implant. More preferably the extended therapeutic effect persists for at least 60 days after release of all or all substantially all of an active agent in vivo from an intraocular implant.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

"Inflammation-mediated" in relation to an ocular condition means any condition of the eye which can benefit or potentially benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic, ophthalmia, Vogt Koyanagi-Harada (VKH) syndrome, histoplasmosis, and uveal effusion.

"Injury" or "damage" are interchangeable and refer to the cellular and morphological manifestations and symptoms resulting from an inflammatory-mediated condition, such as, for example, inflammation.

"Measured under infinite sink conditions in vitro," means assays to measure drug release in vitro, wherein the experiment is designed such that the drug concentration in the receptor medium never exceeds 5% of saturation. Examples of suitable assays may be found, for example, in USP 23; NF 18 (1995) pp. 1790-1798.

"Ocular condition" means a disease, ailment or condition which affects or involves the eye or one or the parts or regions of the eye, such as a retinal disease. The eye includes the eyeball and the tissues and fluids which constitute the eyeball, the periocular muscles (such as the oblique and rectus muscles) and the portion of the optic nerve which is within or adjacent to the eyeball.

"Retinopathy" means a disorder or disease of the retina. Such an disease or disorder may be associated with an overlying condition such as glaucoma, macular edema, dry and wet macular degeneration, diabetic retinopathy, at the like.

"Posterior ocular condition" means a disease, ailment or condition which affects or involves a posterior ocular region or site such as choroid or sclera (in a position posterior to a plane through the posterior wall of the lens capsule), vitreous, vitreous chamber, retina, optic nerve (including the optic disc), and blood vessels and nerve which vascularize or innervate a posterior ocular region or site.

"Steroidal anti-inflammatory agent" and "glucocorticoid" are used interchangeably herein, and are meant to include steroidal agents, compounds or drugs which reduce inflammation when administered at a therapeutically effective level.

"Substantially" means at least 51%. A release of substantially all of an active agent occurs when, at least 24 hours after in vivo insertion of an intraocular implant, a therapeutic amount of the active agent is not present in the vitreous. A release of essentially all of an active agent is deemed to occur when, at least 24 hours after in vivo insertion of an intraocular implant, a detectable amount of the active agent is not present in the vitreous. "Substantially" in relation to the blending, mixing or dispersing of an active agent in a polymer, as in the phrase "substantially homogenously dispersed" means that there are no or essentially no particles (i.e. aggregations) of active agent in such a homogenous dispersal.

"Suitable for insertion (or implantation) in (or into) an ocular region or site" with regard to an implant, means an implant which has a size (dimensions) such that it can be inserted or implanted without causing excessive tissue damage and without unduly physically interfering with the existing vision of the patient into which the implant is implanted or inserted.

A method according to the present invention can be carried out using an implant suitable for insertion, placement or implantation at an ocular site, such as the vitreous. Suitable implant can be made using the methods and materials set forth in U.S. patent application Ser. No. 10/340,237.

The present invention encompasses a method for treating an ocular condition. The method can have the steps of firstly inserting an implant into an ocular site of a patient with an ocular condition. The implant can be made of an active agent, and a carrier associated with the active agent. The carrier can be a polymer or a bioceramic material. The carried can be associated with the active agent by mixing the active agent and the carrier, dispersing the active agent in the carrier, encapsulating the active agent by the carrier, incorporating the active agent within the carrier, and the like.

The next (second) step in the method can be releasing substantially all of the active agent from the implant. The third step in the method can be obtaining an improvement in the ocular condition at a time when a therapeutic amount of the active agent is not present at the ocular site. A fourth step in the method can be maintaining the improvement in the ocular condition for an extended period of time during which a therapeutic amount of the active agent is not present at the ocular site.

The releasing (second) step can occur over a first period of time X, and the subsequent extended period of time during which an improvement in the ocular condition is maintained, although a therapeutic amount of the active agent is not present at the ocular site, is a second period of time between 0.5× and 100×. The first period of time can be between about 30 days and about 40 days, such as about 35 days. The second period of time can be between about 30 days and about 180 days.

The active agent can be an anti-inflammatory agent and the carrier can be a bioerodible polymer. The implant can have a weight between about 1 µg and about 100 mg. The implant can have no dimension less than about 0.1 mm and no dimension greater than about 20 mm. The implant can have a volume of from about 1 $mm^3$ to about 100 $mm^3$, but preferably the implant has a volume of between about 5-20 $mm^3$.

The improvement of the ocular condition obtained by a method within the scope of the present invention can be determined by observing an improved visual acuity, by observing an improved visual contrast sensitivity, by observing a decreased retinal or choroidal blood vessel leakage, by observing a decreased retinal or macular thickness, or by observing a reduced number of cells in the aqueous or vitreous humor or by determining a reduced flare.

The improvement in the ocular condition can occur at a time when a detectable amount of the active agent is not present at the ocular site. The ocular site can be vitreous and the active agent can be dexamethasone.

Another method within the scope of the present invention is a method for treating a chronic ocular condition by (a) inserting an implant into an ocular site of a patient with an ocular condition, the implant comprising (i) an active agent, and (ii) a carrier associated with the active agent; (b) releasing substantially all of the active agent from the implant; (c) obtaining an improvement in the ocular condition at a time when a therapeutic amount of the active agent is not present at the ocular site, and; (d) maintaining the improvement in the ocular condition for an extended period of time during which a therapeutic amount of the active agent is not present at the ocular site.

A further method within the scope of the present invention is a method for treating an inflammatory posterior ocular condition by (a) inserting a biodegradable implant into a posterior ocular site of a patient with an inflammatory posterior ocular condition, the biodegradable implant comprising (i) an anti-inflammatory active agent mixed with (ii) a biodegradable polymer; (b) releasing substantially all of the anti-inflammatory active agent from the biodegradable implant; (c) obtaining an improvement in the inflammatory posterior ocular condition at a time when a therapeutic amount of the anti-inflammatory active agent is not present at the posterior ocular site, and; (d) maintaining the improvement in the inflammatory ocular condition for an extended period of time during which a therapeutic amount of the anti-inflammatory active agent is not present at the posterior ocular site. The inserting step is preferably carried out by insertion of the implant through the pars plana and adjacent thereto in the vitreous cavity. Alternately, the insertion step can be carried out by placing the biodegradable implant into the vitreous about 2 mm to about 6 mm anterior of the macular and not along the visual axis of incoming light through the pupil.

A detailed method within the scope of the present invention is a method for treating persistent macular edema (a) inserting a biodegradable implant deep into the vitreous of a patient with persistent macular edema, the biodegradable implant comprising (i) dexamethasone mixed with (ii) a bioerodible PLGA co-polymer; (b) releasing all of the dexamethasone from the biodegradable implant; (c) obtaining an improvement in the persistent macular edema at a time when a therapeutic amount of the dexamethasone is not present in the vitreous, and; (d) maintaining the improvement in the persistent macular edema for an extended period of time during which a therapeutic amount of the dexamethasone is not present in the vitreous. The inserting step is preferably carried out by insertion of the implant through the pars plana and adjacent thereto in the vitreous cavity. Alternately, the insertion step can be carried out by placing the biodegradable implant into the vitreous about 2 mm to about 6 mm anterior of the macular and not along the visual axis of incoming light through the pupil. The releasing step can comprise releasing between about 350-700 µg of dexamethasone from the biodegradable implant. Additionally, the releasing step can entail releasing about 700 µg of dexamethasone from the biodegradable implant within about 30 days to 40 days after the inserting step. Notably, the obtaining step can comprise obtaining an improvement in the visual acuity of the patient. The improvement in the visual acuity of the patient can be obtained within about 30 days to about 180 days after the inserting step. Significantly, the maintaining step, by which the improvement in the visual acuity of the patient with persistent macular edema can be maintained for an extended period of time during which a therapeutic amount of the dexamethasone is not present in the vitreous, is a period of time of about 30 days to about 150 days after the obtaining step.

A preferred method within the scope of the present invention is a method for improving the visual acuity of a patient with persistent macular edema by (a) inserting a biodegradable implant into the vitreous of a patient with persistent macular edema by inserting the biodegradable implant through the pars plana and adjacent thereto in the vitreous cavity or alternately, the insertion step can be carried out by placing the biodegradable implant into the vitreous about 2 mm to about 6 mm anterior of the macular and not along the visual axis of incoming light through the pupil, the biodegradable implant comprising (i) about 350-700 µg dexamethasone mixed with (ii) a bioerodible PLGA co-polymer; (b) releasing the 350-700 µg of dexamethasone from the biodegradable implant within about 30 days to about 40 days after the inserting step; (c) obtaining an improvement in the visual acuity of the patient with the persistent macular edema at a time within about 30 days and 180 days after the inserting step during which time when a therapeutic amount of the dexamethasone is not present in the vitreous, and; (d) maintaining the improvement in the visual acuity of the patient with the persistent macular edema for about 30 days to about 150 days after the obtaining step during a time when a therapeutic amount of the dexamethasone is not present in the vitreous.

The present invention also includes a method for treating an ocular condition by inserting an implant into the vitreous cavity of a patient with an ocular condition, the implant comprising (i) a steroid, and (ii) a carrier associated with the steroid; followed by releasing substantially all of the steroid from the implant, and then obtaining an improvement in the ocular condition with no increase in intraocular pressure in the patient above about 25 mm Hg, where the patient had a baseline (i.e. prior to implant insertion) IOP of less or equal to about 25 mm Hg.

The present invention also includes a method for treating an ocular condition by inserting an implant into the vitreous cavity of a patient with an ocular condition, the implant comprising (i) a steroid, and (ii) a carrier associated with the steroid; followed by releasing substantially all of the steroid from the implant, and then obtaining an improvement in the ocular condition with no occurrence of an ocular cataract in the patient subsequent to insertion of the implant.

DRAWINGS

DESCRIPTION

Figure 1:
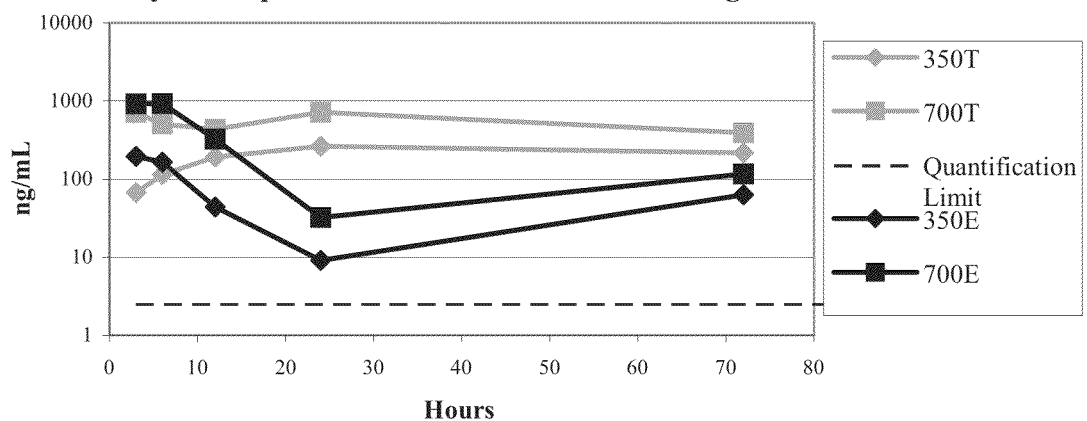
FIG. 1 is a graph showing vitreous humor concentrations (ng/ml) of dexamethasone over a period of 72 hours for two tabletted implants (350 μg or 700 μg of dexamethasone) and for two extrusion formed implants (350 μg or 700 μg of dexamethasone).

The present invention is based upon the discovery of methods for obtaining and for maintaining a therapeutic treatment of an ocular condition during a period of time during which a therapeutic amount of an active agent is not present. A method within the scope of the present invention can be carried out by inserting an implant comprising an active agent into an ocular site of a patient. Over a first period of time the implant then releases all of it's active agent. There is then obtained an amelioration of a manifestation or of a symptom of the ocular condition (i.e. a therapeutic effect) for a second period of time during which a detectable or therapeutic amount of the active agent is not present at the ocular site.

It is generally accepted that treatment of a chronic ocular condition requires chronic administration of a therapeutic amount of a suitable active agent. Glaucoma is a chronic ocular condition characterized by high (i.e. greater than 25 mm Hg) intra ocular (aqueous humor) pressure. It is known that if a patient receiving topical (i.e. applied as eye drops) anti-glaucoma medication stops using the topical anti-glaucoma medication his intraocular pressure ("IOP") will quickly revert to its former (baseline) high (unmedicated) intraocular pressure raise. The period for return to baseline IOP is referred to as the washout period. Well before the conclusion of the washout period (i.e. usually after a few hours or at most a few days) of time there is no longer a therapeutic amount or a detectable amount of the active agent in question present for treatment of the ocular condition. Thus the term washout refers to the time period required for return to substantially a baseline (pre-therapeutic) condition, not to the time period required for removal of the active agent. The washout period for topical beta-blocker anti-glaucoma medication is about four weeks. The washout period for topical sympathomimetics (stimulating alpha and beta receptors; i.e. epinephrine) anti-glaucoma medication is about three weeks. The washout period for topical miotics (i.e. pilocarpine) anti-glaucoma medication is about 48 hours. Marcon, I., *A double-masked comparison of betaxolol and levobunolol for the treatment of primary open-angle glaucoma*, Arq Bras Oftalmol 1990; 53(1):27-32.

Additionally, it is known that the washout period for topical carbonic anhydrase inhibitor (i.e. dorzolamide) anti-glaucoma medication is two to four weeks, and that the washout period for alpha adrenergic receptor agonists (i.e. brimonidine) is also about two to four weeks. Molfino, F., et al., *IOP-lowering effect of dorzolamide 2% versus brimonidine tartrate 0.2%. A prospective randomized cross over study*, Invest Ophthalmol Vis Sci 1998 Mar. 15; 39(4):S481. The washout period for brimonidine may be as long as five weeks and as long as eight weeks for a prostaglandin (i.e. latanoprost) anti-glaucoma medication. Stewart, W., et al., *Washout periods for brimonidine 0.2% and latanoprost 0.005%*, Am J Ophthalmol 2001 June; 131(6):798-799.

To confirm and to supplement the existence of washout periods, three different population of patients with glaucoma were examined, as set forth by Example A, supra. The results set forth by Example A show that within a short period of a day or two after stopping chronic use of various anti-glaucoma medications, the mean intraocular pressure of all patient populations increased significantly, thereby showing that a chronic intraocular condition requires chronic treatment to obtain an ongoing therapeutic effect.

Thus, it was surprising and unexpected to discover that methods within the scope of the present invention permit ongoing therapeutic treatment of a chronic ocular condition for an extended period of time after the washout period— when both a therapeutic level of the active agent is (long since) no longer present and by which time it was expected that a return or a substantial return to a baseline condition (i.e. as assessed prior to commencement of therapy) should have occurred in the patients. Specifically, prior to the present invention it was thought that continuous and prolonged therapy (i.e. chronic active agent [i.e. steroid] administration) was required to treat a chronic ocular condition.

The present invention thereby permits an ocular condition to be treated with use of less active agent for a shorter duration with fewer side effects and complications, as compared to a treatment of the same ocular condition with the same active agent administered as a non-implant formulation (i.e. as a liquid intravitreal injection). Thus, the present invention permits a short term treatment (i.e. release of an active agent from an intra-vitreal implant over 10-40 days) to provide a long term therapeutic benefit (i.e. for 150 days or longer after all the active agent has been released from the implant) with fewer side effects and fewer complications due to removal of the need for chronic dosing. Thus a desired clinical (therapeutic) effect such as lower IOP, less inflammation, decreased retinal thickness, increased visual acuity, increased visual contract sensitivity, reduced retinal and/or choroidal blood vessel leakage can be obtained and maintained for an extended period of time (i.e. about 6 months or longer) after intra-vitreal release (i.e. after a sustained release over 10-40 days) of all the active agent.

The present invention encompasses biodegradable ocular implants and implant systems and methods of using such implants and implant systems for treating posterior ocular conditions. The implants can be formed to be monolithic, that is the active agent is homogenously distributed or dispersed throughout the biodegradable polymer matrix. Additionally, the implants can be formed to release an active agent into an ocular region of the eye over various time periods. Thus, the active agent can be released from implants made according to the present invention for a period of time of, for example, 30-40 days.

Biodegradable Implants for Treating an Ocular Condition

The implants of the present invention can include an active agent mixed with or dispersed within a biodegradable polymer. The implant compositions can vary according to the preferred drug release profile, the particular active agent used, the ocular condition being treated, and the medical history of the patient. Active agents that may be used include, but are not limited to (either by itself in an implant within the scope of the present invention or in combination with another active agent): ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxacillin, oxacillin, methicillin; lincosamides such as lincomycin; polypeptide antibiotics such as polymixin polymyxin and bacitracin; tetracyclines such as tetracycline; quinolones such as ciproflaxin, ciprofloxacin, etc.; sulfonamides such as chloramine T; and sulfones such as sulfanilic acid as the hydrophilic entity, anti-viral drugs, e.g. acyclovir, gancyclovir, ganciclovir, vidarabine, azidothymidine, dideoxyinosine, dideoxycytosine, dexamethasone, ciproflaxin, ciprofloxacin, water soluble antibiotics, such as acyclovir, gancyclovir, ganciclovir, vidarabine, azidothymidine, dideoxyinosine, dideoxycytosine; epinephrine; isoflurphate; isoflurophate; adriamycin; bleomycin; mitomycin; ara-C; actinomycin D; scopolamine; and the like, analgesics, such as codeine, morphine, ketorolac, naproxen, etc., an anesthetic, e.g. lidocaine; β-adrenergic blocker or β-adrenergic agonist, e.g. ephedrine, epinephrine, etc.; aldose reductase inhibitor, e.g. epalrestat, ponalrestat, sorbinil, tolrestat; anti-allergic, e.g. cromolyn, beclomethasone, dexamethasone, and flunisolide; colchicine, anthelmintic agents, e.g. ivermectin and suramin sodium; antiamoebic agents, e.g. chloroquine and chlortetracycline; and antifungal agents, e.g. amphotericin, etc., anti-angiogenesis compounds such as anecortave acetate, retinoids such as Tazarotene, anti-glaucoma agents, such as brimonidine (Alphagan and Alphagan P), acetazolamide, bimatoprost (Lumigan), Timolol, levobunolol; memantine; alpha-2 adrenergic receptor agonists; 2ME2; anti-neoplastics, such as vinblastine, vincristine, interferons; alpha., beta. and γ, antimetabolites, such as folic acid analogs, purine analogs, and pyrimidine analogs; immunosuppressants such as azathioprine, cyclosporine and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like.

In one variation the active agent is methotrexate. In another variation, the active agent is a retinoic acid. In another variation, the active agent is an anti-inflammatory agent such as a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a further variation, the anti-inflammatory agent is a steroidal anti-inflammatory agent, such as dexamethasone.

Steroidal Anti-Inflammatory Agents

The steroidal anti-inflammatory agents that may be used in the ocular implants include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one embodiment, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the biodegradable implant includes a combination of two or more steroidal anti-inflammatory agents.

The active agent, such as a steroidal anti-inflammatory agent, can comprise from about 10% to about 90% by weight of the implant. In one variation, the agent is from about 40% to about 80% by weight of the implant. In a preferred variation, the agent comprises about 60% by weight of the implant. In a more preferred embodiment of the present invention, the agent can comprise about 50% by weight of the implant.

Biodegradable Polymers

In one variation, the active agent can be homogeneously dispersed in the biodegradable polymer of the implant. The implant can be made, for example, by a sequential or double extrusion method. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the implant.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen can be present as amide, cyano, and amino. An exemplary list of biodegradable polymers that can be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA copolymers are used. In other variations, PLGA copolymers are used in conjunction with polylactide polymers.

Biodegradable polymer matrices that include mixtures of hydrophilic and hydrophobic ended PLGA may also be employed, and are useful in modulating polymer matrix degradation rates. Hydrophobic ended (also referred to as capped or end-capped) PLGA has an ester linkage hydrophobic in nature at the polymer terminus. Typical hydrophobic end groups include, but are not limited to alkyl esters and aromatic esters. Hydrophilic ended (also referred to as uncapped) PLGA has an end group hydrophilic in nature at the polymer terminus. PLGA with a hydrophilic end groups at the polymer terminus degrades faster than hydrophobic ended PLGA because it takes up water and undergoes hydrolysis at a faster rate (Tracy et al., *Biomaterials* 20:1057-1062 (1999)). Examples of suitable hydrophilic end groups that may be incorporated to enhance hydrolysis include, but are not limited to, carboxyl, hydroxyl, and polyethylene glycol. The specific end group will typically result from the initiator employed in the polymerization process. For example, if the initiator is water or carboxylic acid, the resulting end groups will be carboxyl and hydroxyl. Similarly, if the initiator is a monofunctional alcohol, the resulting end groups will be ester or hydroxyl.

Additional Agents

Other agents may be employed in the formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The biodegradable ocular implants can also include additional hydrophilic or hydrophobic compounds that accelerate or retard release of the active agent. Additionally, release modulators such as those described in U.S. Pat. No. 5,869,079 can be included in the implants. The amount of release modulator employed will be dependent on the desired release profile, the activity of the modulator, and on the release profile of the glucocorticoid in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

Release Kinetics

An implant within the scope of the present invention can be formulated with an active agent (or a prodrug of an active agent) dispersed within a biodegradable polymer matrix. Without being bound by theory, it is believed that the release of the active agent can be achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, and the erosion rate of the polymer(s). The release kinetics achieved by this form of active agent release are different than that achieved through formulations which release active agents through polymer swelling, such as with crosslinked hydrogels. In that case, the active agent is not released through polymer erosion, but through polymer swelling and drug diffusion, which releases agent as liquid diffuses through the pathways exposed.

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release.

The release kinetics of the implants of the present invention can be dependent in part on the surface area of the implants. A larger surface area exposes more polymer and active agent to ocular fluid, causing faster erosion of the polymer matrix and dissolution of the active agent particles in the fluid. Therefore, the size and shape of the implant may also be used to control the rate of release, period of treatment, and active agent concentration at the site of implantation. At equal active agent loads, larger implants will deliver a proportionately larger dose, but depending on the surface to mass ratio, may possess a slower release rate. For implantation in an ocular region, the total weight of the implant preferably ranges, e.g., from about 200-15000 µg, usually from about 1000-5000 µg. In one variation, the total weight of the implant is about 1200 to about 1,800 µg. In another variation, the total weight of the implant is about 2400 to about 3,600 µg. Preferably, the implant has a weight between about 100 µg and about 2 mg.

The bioerodible implants are typically solid, and may be formed as particles, sheets, patches, plaques, films, discs, fibers, rods, and the like, or may be of any size or shape compatible with the selected site of implantation, as long as the implants have the desired release kinetics and deliver an amount of active agent that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In one variation, the rods have diameters of about 0.1 mm to about 1 mm. In another variation, the rods have diameters of about 0.3 mm to about 0.75 mm. In yet a further variation, other implants having variable geometries but approximately similar volumes may also be used.

The proportions of active agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the drug delivery device is added to a measured volume of a solution containing 0.9% NaCl in water, where the solution volume will be such that the drug concentration is after release is less than 20%, and preferably less than 5%, of saturation. The mixture is maintained at 37° C. and stirred slowly to ensure drug diffusion after bioerosion. The appearance of the dissolved drug as a function of time may be followed by various methods known in the art, such as spectrophotometrically, HPLC, mass spectroscopy, etc.

Applications

Examples of ocular conditions which can be treated by the implants and methods of the invention include, but are not limited to, glaucoma, uveitis, macular edema, macular degeneration, retinal detachment, ocular tumors, bacterial, fungal or viral infections, multifocal choroiditis, diabetic retinopathy, proliferative vitreoretinopathy (PVR), sympathetic ophthalmia, Vogt Koyanagi-Harada (VKH) syndrome, histoplasmosis, uveal diffusion, and vascular occlusion. In one variation, the implants are particularly useful in treating such medical conditions as uveitis, macular edema, vascular occlusive conditions, proliferative vitreoretinopathy (PVR), and various other retinopathies.

Methods of Implantation

The biodegradable implants can be inserted into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The method of implantation generally first involves accessing the target area within the ocular region with the needle, trocar or implantation device. Once within the target area, e.g., the vitreous cavity, a lever on a hand held device can be depressed to cause an actuator to drive a plunger forward. As the plunger moves forward, it can push the implant or implant into the target area (i.e. the vitreous).

Methods for Making Implants

Various techniques may be employed to make implants within the scope of the present invention. Useful techniques include phase separation methods, interfacial methods, extrusion methods, compression methods, molding methods, injection molding methods, heat press methods and the like.

Choice of the technique, and manipulation of the technique parameters employed to produce the implants can influence the release rates of the drug. Room temperature compression methods result in an implant with discrete microparticles of drug and polymer interspersed. Extrusion methods result in implants with a progressively more homogenous dispersion of the drug within a continuous polymer matrix, as the production temperature is increased.

The use of extrusion methods allows for large-scale manufacture of implants and results in implants with a homogeneous dispersion of the drug within the polymer matrix. When using extrusion methods, the polymers and active agents that are chosen are stable at temperatures required for manufacturing, usually at least about 50° C. Extrusion methods use temperatures of about 25° C. to about 150° C., more preferably about 60° C. to about 130° C.

Different extrusion methods may yield implants with different characteristics, including but not limited to the homogeneity of the dispersion of the active agent within the polymer matrix. For example, using a piston extruder, a single screw extruder, and a twin screw extruder will generally produce implants with progressively more homogeneous dispersion of the active. When using one extrusion method, extrusion parameters such as temperature, extrusion speed, die geometry, and die surface finish will have an effect on the release profile of the implants produced.

In one variation of producing implants by a piston extrusion methods, the drug and polymer are first mixed at room temperature and then heated to a temperature range of about 60° C. to about 150° C., more usually to about 130° C. for a time period of about 0 to about 1 hour, more usually from about 0 to about 30 minutes, more usually still from about 5 minutes to about 15 minutes, and most usually for about 10 minutes. The implants are then extruded at a temperature of about 60° C. to about 130° C., preferably at a temperature of about 75° C.

In an exemplary screw extrusion method, the powder blend of active agent and polymer is added to a single or twin screw extruder preset at a temperature of about 80° C. to about 130° C., and directly extruded as a filament or rod with minimal residence time in the extruder. The extruded filament or rod is then cut into small implants having the loading dose of active agent appropriate to treat the medical condition of its intended use.

Implant systems according to the invention can include a combination of a number of bioerodible implants, each having unique polymer compositions and drug release profiles that when co-administered provide for an extended continuous release of drug. Examples of fast release implants include those made of certain lower molecular weight, fast degradation profile polylactide polymers, such as R104 made by Boehringer Ingelheim GmbH, Germany, which is a poly(D,L-lactide) with a molecular weight of about 3,500. Examples of medium release implants include those made of certain medium molecular weight, intermediate degradation profile PLGA co-polymers, such as RG755 made by Boehringer Ingelheim GmbH, Germany, which is a poly(D,L-lactide-co-glycolide with wt/wt 75% lactide:25% glycolide, a molecular weight of about 40,000 and an inherent viscosity of 0.50 to 0.70 dl/g. Examples of slow release implants include those made of certain other high molecular weight, slower degradation profile polylactide polymers, such as R203/RG755 made by Boehringer Ingelheim GmbH, Germany, for which the molecular weight is about 14,000 for R203 (inherent viscosity of 0.25 to 0.35 dl/g) and about 40,000 for RG755.

Examples of implants include those formed with RG755, R203, RG503, RG502, RG 502H RG502H as the first polymer, and RG502, RG502H as the second polymer. Other polymers that can be used include PDL (poly(D,L-lactide)) and PDLG (poly(D,L-lactide-co-glycolide)) polymers available from PURAC America, Inc. Lincolnshire, Ill. Poly(caprolactone) polymers can also be used. The characteristics of the specified polymers are (1) RG755 has a molecular weight of about 40,000, a lactide content (by weight) of 75%, and a glycolide content (by weight) of 25%; (2) R203 has a molecular weight of about 14,000, and a 100%; (30 RG503 has a molecular weight of about 28,000, a lactide content of 50%, and a glycolide content of 50%; (4) RG502 has a molecular weight of about 11,700 (inherent viscosity of 0-16 to 0.24 dl/g), a lactide content of 50%, and a glycolide content of 50%, and; (5) RG502H has a molecular weight of about 8,500, a lactide content of 50%, a glycolide content of 50% and free acid at the end of polymer chain.

Generally, if inherent viscosity is 0.16 the molecular weight is about 6,327, and if the inherent viscosity is 0.28 the molecular weight is about 20670.

According to our invention continual or substantially continual release of drug at levels corresponding to at least 10 ng/ml of dexamethasone or dexamethasone equivalent for between about 5-40 days can be achieved.

Figure 5:
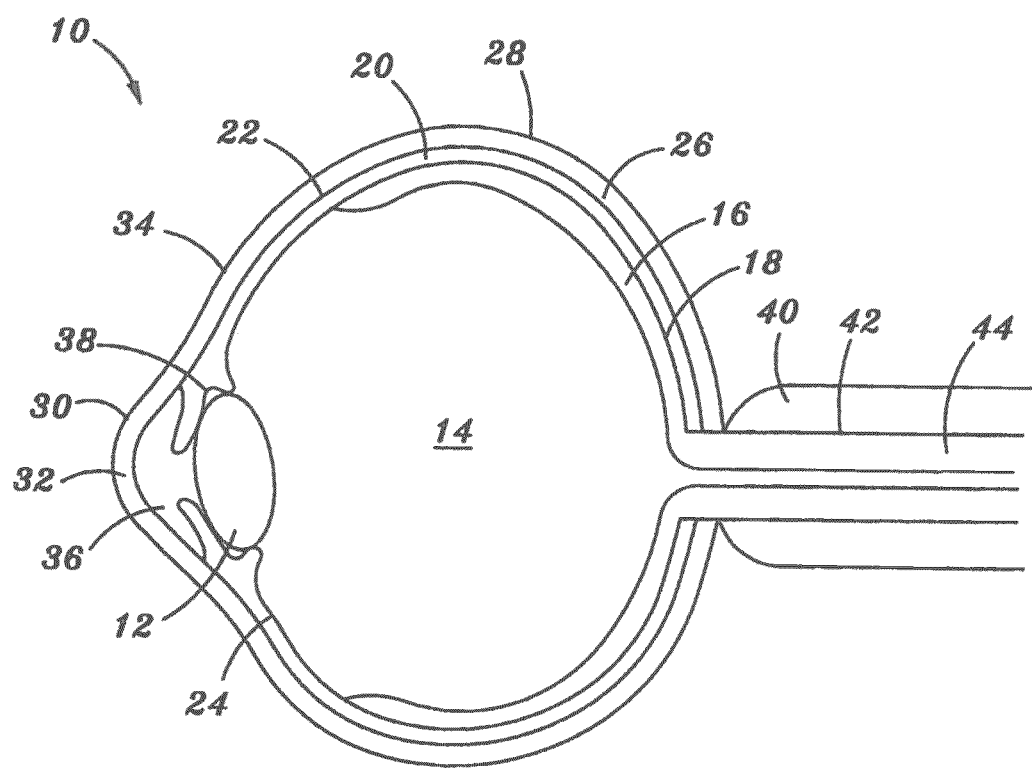
FIG. 5 illustrates diagrammatically a cross-sectional view of an eye.

This may be more clearly understood with reference to FIG. 5 which illustrates a cross-sectional view of a human eye 10 in order to illustrate the various sites that may be suitable for implantation of an implant in accordance with the present invention.

The eye 10 comprises a lens 12 and encompasses the vitreous chamber 14. Adjacent to the vitreous chamber is the optic part of the retina 16. Implantation may be into the vitreous 14, intraretinal 16 or subretinal 18. The retina 16 is surrounded by the choroid 20. Implantation may be intrachoroidal or suprachoroidal 22. Between the optic part of the retina and the lens, adjacent to the vitreous, is the pars plana 24. Surrounding the choroid 20 is the sclera 26. Implantation may be intrascleral 26 or episcleral 28. The external surface of the eye is the cornea 30. Implantation may be epicorneal 30 or intra-corneal 32. On the external surface of the eye is the conjunctiva 34. Behind the cornea is the anterior chamber 36, behind which is the lens 12. The posterior chamber 38 surrounds the lens, as shown in the figure. Opposite from the external surface is the optic nerves, and the arteries and vein of the retina. Implants into the meningeal spaces 40, the optic nerve 42 and the intraoptic nerve 44 allows for drug delivery into the central nervous system, and provide a mechanism whereby the blood-brain barrier may be crossed.

Other sites of implantation include the delivery of antitumor drugs to neoplastic lesions, e.g. tumor, or lesion area, e.g. surrounding tissues, or in those situations where the tumor mass has been removed, tissue adjacent to the previously removed tumor and/or into the cavity remaining after removal of the tumor. The implants may be administered in a variety of ways, including surgical means, injection, trocar, etc.

EXAMPLES

The following examples illustrate aspects and embodiments of the invention.

Example A

Rapid Loss of Therapeutic Effect Upon Cessation of Ocular Medication

To examine loss or reduction of a therapeutic effect (i.e. IOP lowering) upon cessation of chronic medication administration used to treatment a chronic ocular condition, three different populations of patients with glaucoma were examined.

1. A population of twenty patients with glaucoma was examined. It was determined that on day 28 after the patients had been receiving topical Lumigan 0.03% once a day for three weeks and then twice a day for one week, the mean IOP on day 28 was −8 mm Hg from baseline. Yet on day 30 after 2 days with no medication administered it was determined that the mean IOP of the 20 patients was only −6 mm Hg from baseline.

2. Similarly for a separate population of 20 patients with glaucoma it was determined that on day 28 after the patients had been receiving topical timolol 0.5% twice a day for four weeks, the mean IOP on day 28 was −4 mm Hg from baseline. Yet on day 30 after 2 days with no medication administered the mean IOP of the 20 patients was only −2 mm Hg from baseline.

3. For a separate (third) population of 18 patients with glaucoma it was determined that on day 14 after the patients had been receiving topical brimonidine for 14 days, the mean IOP on day 14 was −2 mm Hg from baseline. Yet on day 15 after 24 hours with no medication administered the mean IOP of the 18 patients was only −0.8 mm Hg from baseline.

The results set forth by Example A show that within a short period of a day or two after stopping chronic use of various anti-glaucoma medications, the mean intraocular pressure of all patient populations increased significantly, thereby showing that a chronic intraocular condition requires chronic treatment to obtain an ongoing therapeutic effect.

Example 1

Manufacture of Compressed Tablet Implants

Micronized dexamethasone (Pharmacia, Peapack, N.J.) and micronized hydrophobic end 50/50 PLGA (Birmingham Polymers, Inc., Birmingham, Ala.) were accurately weighed and placed in a stainless steel mixing vessel. The vessel was sealed, placed on a Turbula mixer and mixed at a prescribed intensity, e.g., 96 rpm, and time, e.g., 15 minutes. The resulting powder blend was loaded one unit dose at a time into a single-cavity tablet press. The press was activated at a pre-set pressure, e.g., 25 psi, and duration, e.g., 6 seconds, and the tablet was formed and ejected from the press at room temperature. The ratio of dexamethasone to PLGA was 70/30 w/w for all compressed tablet implants.

Example 2

Manufacture of Extruded Implants

Micronized dexamethasone (Pharmacia, Peapack, N.J.) and unmicronized PLGA were accurately weighed and placed in a stainless steel mixing vessel. The vessel was sealed, placed on a Turbula mixer and mixed at a prescribed intensity, e.g., 96 rpm, and time, e.g., 10-15 minutes. The unmicronized PLGA composition comprised a 30/10 w/w mixture of hydrophilic end PLGA (Boehringer Ingelheim, Wallingford, Conn.) and hydrophobic end PLGA (Boehringer Ingelheim, Wallingford, Conn.). The resulting powder blend was fed into a DACA Microcompounder-Extruder (DACA, Goleta, Calif.) and subjected to a pre-set temperature, e.g., 115° C., and screw speed, e.g., 12 rpm. The filament was extruded into a guide mechanism and cut into exact lengths that corresponded to the designated implant weight. The ratio of dexamethasone to total PLGA (hydrophilic and hydrophobic end) was 60/40 w/w for all extruded implants.

Thus, the implant is composed of dexamethasone and a PLGA [poly(D,L-lactide-co glycolide)] polymer matrix.

There are two sizes of the implant: one containing about 350 μg of dexamethasone and one containing about 700 μg of dexamethasone. Both sizes of implant contain 60% by weight of drug and 40% by weight of polymer.

As set forth above, the implants can be manufactured by a continuous extrusion process by double extrusion using a twin-screw extruder. The implants can have a microstructure consisting of a micronized dexamethasone particles homogeneously dispersed in a continuous polymer matrix.

The implants can be approximately cylindrical in shape. The 700 μg implants can have a diameter of about 460 μm (0.460 mm) and a length of about 6 mm, and the 350 μg implant can have the same diameter and a length of about 3 mm.

The total weight of the 700 μg implants can be about 1.2 mg and the total weight of the 350 μg implant can be about 0.6 mg. Weight tolerance for a population of implants can be about +10% by weight or less.

The PLGA polymer matrix can be a mixture of acid end and ester end polymers. PLGA molecules are terminated at one end by an -OH (hydroxyl) group and at the other end by a —COOR group where for acid end molecules R=H and for ester end molecules R=alkyl. The PLGA used in the Posurdex™ implant can be a mixture of 75% by weight acid end PLGA and 25% by weight ester end PLGA. That is, the implants will be about 60% by weight drug, about 30% by weight acid end PLGA, and about 10% by weight ester end PLGA. Both acid and ester end PLGA will contain 50% lactide units and 50% glycolide units.

Example 3

Method and Devices for Placing Implants into the Vitreous

Implants were placed into the posterior segment of the right eye of New Zealand White Rabbits by incising the conjunctiva and sclera between the 10 and 12 o'clock positions with a 20-gauge microvitreoretinal (MVR) blade. Fifty to 100 μl, of vitreous humor was removed with a 1-cc syringe fitted with a 27-gauge needle. A sterile trocar, preloaded with the appropriate implant (drug delivery system, DDS), was inserted 5 mm through the sclerotomy, and then retracted with the push wire in place, leaving the implant in the posterior segment. Sclerae and conjunctivae were than closed using a 7-0 Vicryl suture. Suitable applicators which have been used to place implants of Examples 1 and 2 in the vitreous of human eyes are set forth in U.S. patent application Ser. No. 10/666,872.

Example 4

Comparison of Tablet and Extruded Dexamethasone Bioerodible Vitreal Implants Over 72 Hours Examples 4 and 5 set forth a pre-clinical study carried out to evaluate biodegradable polymeric implants inserted in the posterior chamber (i.e. in the vitreous) of an eye. The implant contained the anti-inflammatory steroid dexamethasone as the active agent. These implant are referred to below a "DEX PS DDS" implants. These implants and can be made as a tablet ("T") or as an extrusion ("E"), using a continuous extrusion process.

The dexamethasone can be used as the acetate salt or in the form of the sodium phosphate ester. In ophthalmology dexamethasone sodium phosphate has been widely used for over 40 years as a topically applied solution (0.1%). The maximum safe dose of dexamethasone for intravitreal injection or for release from an implanted sustained-release devices is believed to be about 4,800 μg to 5,000 μg. Thus, the total dose of 350 μg or 700 μg delivered with the DEX PS DDS is a non-toxic dose. The test implant DEX PS DDS is a polymeric matrix designed to deliver dexamethasone in vivo over a time period of approximately 35 days.

As set forth below, two animal studies were carried out (a 72 hour study and an 84 day study), with the DEX PS DDS, using both a tablet (tableted implant) and an extruded form of the implant, to evaluate the intraocular and systemic pharmacokinetics (PK) of this intraocular drug delivery system.

These experiments showed that both the tableted and extruded dosage forms can release 700 μg or 350 μg of dexamethasone over about the 35 days it takes the implant to bioerode.

A 72 hour experiment was carried out to compare the pharmacokinetics of tableted and extruded forms at two dose levels of DEX PS DDS® upon implantation into the posterior segment (vitreous) of the eyes of New Zealand white rabbits.

The four types of implants used in this experiment were designated as 350 μg extruded DEX PS DDS ("350E"), 700 μg extruded DEX PS DDS ("700E"), 350 μg tableted DEX PS DDS ("350T") and 700 μg tableted DEX PS DDS ("700T").

On Day 0, 120 male New Zealand white rabbits each received 1 of the 4 types of test implants (30 rabbits per test implant) in the posterior segment (vitreous) of the right eye. The left eye of each animal served as a control. Euthanasia and necropsy were performed at 3, 6, 12, 24, and 72 hours after dosing. Prior to euthanasia, plasma was collected for evaluation of plasma dexamethasone concentrations. Aqueous and vitreous humor samples were collected from the test and control eyes at necropsy, and the vitreous humor sample was divided into two sections. The experiment was carried out in compliance with Good Laboratory Practice (GLP Regulations, 21 CFR, Part 58). The section of the vitreous humor containing the DEX PS DDS remnant(s) was analyzed for dexamethasone concentrations and vitreous humor and aqueous humor of the treated eye were assayed for dexamethasone concentrations, as was the vitreous and the aqueous humor of the control eye, and the plasma.

No mortality occurred following implantation of the DEX PS DDS. Anesthesia and surgical recovery led to minor weight loss in 28 of 48 animals necropsied at 24 and 72 hours, but no other morbidity was reported during the experiment.

As shown by FIG. 1 concentration profiles in the vitreous humor were similar for the 350E and 700E implants of DEX PS DDS, with peak mean vitreous humor concentrations observed at 3 hours (194.65 ng/mL and 912.33 ng/mL, respectively) and 6 hours (163.40 ng/mL and 918.50 ng/mL, respectively).

Mean dexamethasone concentrations with the extruded dosage form were considerably higher for the 700 μg dose level than for the 350 μg dose level. Between 6 and 24 hours, dexamethasone concentrations declined, and then, for the extruded implants, increased from 24 to 72 hours. This pattern of drug release suggests that the initial concentrations of dexamethasone observed in the vitreous resulted from surface release of dexamethasone, which led to early peak mean concentrations. This initial peak in concentration was followed by a decline in mean drug concentration and then an increase in drug concentration with the initiation of dexamethasone release from the polymer matrix (see FIG. 1).

Initial mean vitreous humor dexamethasone concentrations at 3 and 6 hours were lower for the tablet dosage form than the extruded dosage form at both dose levels. However, the tablet dosage form demonstrated higher drug concentrations than the extruded dosage form at all remaining time points (12, 24 and 72 hours) at both dose levels. Overall, peak mean vitreous humor dexamethasone concentrations were similar between the two dosage forms at corresponding dose levels. The mean vitreous humor concentrations for the tablet dosage form within each dose level did not change substantially over the 72-hour study period. Peak mean vitreous humor concentrations of dexamethasone were observed at 24 hours for both the 350T and 700T groups (261.82 ng/mL and 716.33 ng/mL, respectively) (FIG. 1).

Figure 2:
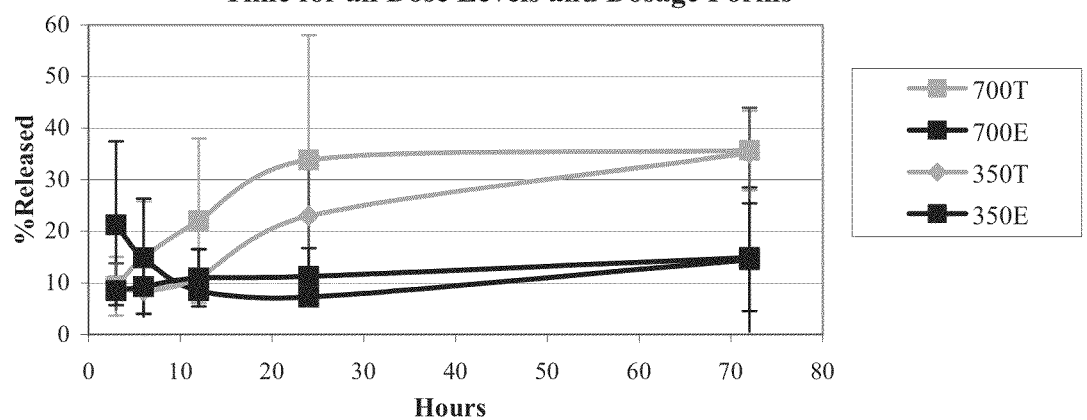
FIG. 2 is a graph showing cumulative percent of dexamethasone released into the vitreous humor over a period of 72 hours for two tabletted implants (350 μg or 700 μg of dexamethasone) and for two extrusion formed implants (350 μg or 700 μg of dexamethasone).

The proportion of dexamethasone released from the DEX PS DDS over the 72-hour study period for the extruded dose levels (350E and 700E) was consistent across both dose levels at approximately 15%. Likewise the tablet dosage form also had similar dexamethasone release profiles for both dose levels (350T and 700T), but released a significantly greater proportion of the total dexamethasone (approximately 35%) by the end of the 72-hour study (FIG. 2).

Consistent with the greater release of dexamethasone from the tablet dosage form during this 72-hour study, higher mean concentrations of drug were measured in the aqueous humor at all sampling points for both the 350T and 700T groups when compared to the 350E and 700E groups. In general, for both dosage forms and dose levels, the mean aqueous humor concentrations of dexamethasone were approximately 10 times lower than the mean vitreous humor concentrations of dexamethasone.

Plasma dexamethasone concentrations were observed at all sampling points for the tablet dosage form, but only minimally above the limit of quantification (1.00 ng/mL). Measurable dexamethasone concentrations were not observed in the plasma of animals in the 350E group, and plasma concentrations were measurable, but at very low concentrations, for the 700E group at 3, 6 and 12 hours.

With a single exception, mean dexamethasone concentrations were below the limit of quantification in the vitreous and aqueous humor of the control eyes for both dosage forms at all dose levels. The exception was observed in the 350T dose control group in which a vitreous humor concentration of 2.98 ng/mL was observed at 6 hours.

Conclusion

Although release profiles were similar among dose levels (350 µg and 700 µg) within each dosage form, the extruded dosage form released approximately 15% of the dose over the study period while the tablet dosage form released approximately 35% over the same period.

The results of this study demonstrate that peak mean vitreous humor concentrations of dexamethasone are similar for the tablet and extruded dosage forms over the 72-hour study period. For both dosage forms the mean concentrations of dexamethasone observed in the vitreous humor, aqueous humor, and plasma were consistent with the dose levels administered.

Example 5

Comparison of Tablet and Extruded Dexamethasone Bioerodible Vitreal Implants Over 84 Days An 84 day experiment was carried out to compare the pharmacokinetics of tableted and extruded forms at two dose levels of DEX PS DDS® upon implantation into the posterior segment (vitreous) of the eyes of New Zealand white rabbits.

This experiment was designed to evaluate the intraocular (vitreous and aqueous humor) and systemic (plasma) pharmacokinetics (PK) of two dosage forms of DEX PS DDS, tableted and extruded, with each dosage form evaluated at two dose levels. The same four test implant types used in Example 1 were used in this experiment: 350 µg extruded DEX PS DDS (350E), 700 µg extruded DEX PS DDS (700E), 350 µg tableted DEX PS DDS (350T) and 700 µg tableted DEX PS DDS (700T).

On Day 0, 312 male New Zealand White rabbits each received 1 of the 4 test implants (78 rabbits per test article) in the posterior segment (vitreous) of the right eye. The left eye of each animal served as a control. Euthanasia and necropsy were performed at Days 1, 3, 7, 14, 21, 28, 35, 45, 56, 70, and 86. Prior to euthanasia, plasma was collected for evaluation of plasma dexamethasone levels. Vitreous humor samples were collected at necropsy, and the vitreous was divided into two sections: the section containing the DEX PS DDS remnant(s) and the remaining vitreous humor section without DEX PS DDS remnants were analyzed.

The experiment was carried out in compliance with Good Laboratory Practice (GLP Regulations, 21 CFR, Part 58). The section of the vitreous humor containing the DEX PS DDS remnant(s) was analyzed for dexamethasone concentrations and vitreous humor and aqueous humor of the treated eye were assayed for dexamethasone concentrations, as was the vitreous and the aqueous humor of the control eye, and the plasma. A subset of twenty-four animals (6 per test implant) underwent weekly ophthalmic examinations to monitor the polymer matrix dissolution of the test article and dissolution was evaluated in all animals with test article implants prior to euthanasia. Dissolution was evaluated by a veterinary ophthalmologist using a numerical grading scale.

No mortality occurred following implantation of the DEX PS DDS. Anesthesia and surgical recovery led to minor weight loss early in the study, however none of the animals necropsied after Day 45 demonstrated an overall weight loss between surgery and necropsy, indicating that any early weight loss was regained.

Figure 3:
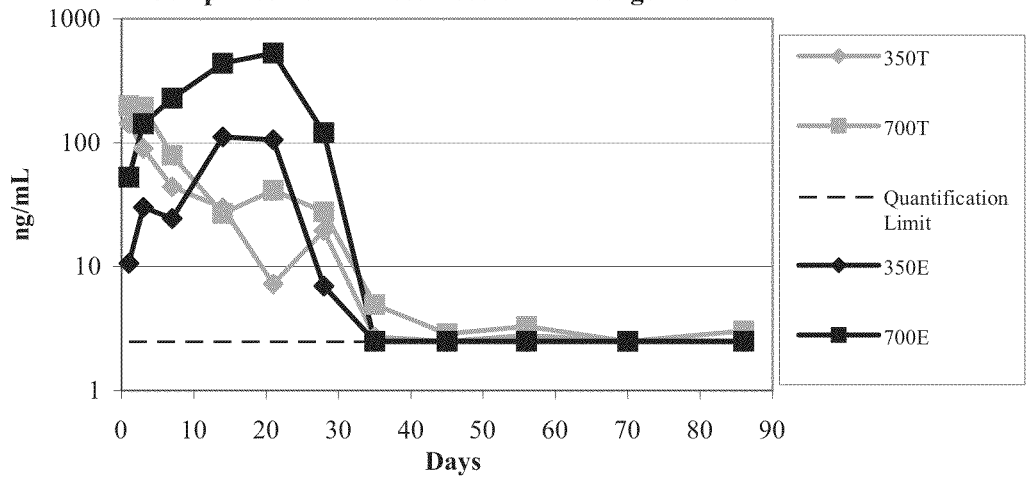
FIG. 3 is a graph showing vitreous humor concentrations (ng/ml) of dexamethasone over a period of 84 days for two tabletted implants (350 μg or 700 μg of dexamethasone) and for two extrusion formed implants (350 μg or 700 μg of dexamethasone).

Vitreous humor concentrations of dexamethasone were observed in the 350E group on Day 1 (10.66 ng/mL) through Day 28 (6.99 ng/mL), with peak mean concentrations at Day 14 (111.30 ng/mL) and Day 21 (105.10 ng/mL). In the 700E group, mean vitreous humor concentrations of dexamethasone were measured from Day 1 (52.63 ng/mL) through Day 28 (119.70 ng/mL), with peak mean concentrations observed on Day 14 (435.60 ng/mL) and Day 21 (527.50 ng/mL). By Day 35, mean concentrations of dexamethasone were at or below the limit of quantification (2.50 ng/mL) for both levels of the extruded dosage form (FIG. 3).

For the 350T group, peak mean dexamethasone concentrations in the vitreous humor were identified on Day 1 (142.20 ng/mL) and Day 3 (89.58 ng/mL), with measurable concentrations observed through Day 56 (2.79 ng/mL). For the 700T group, peak mean dexamethasone concentrations were also observed at Day 1 (198.56 ng/mL) and Day 3 (193.06 ng/mL), with measurable concentrations observed intermittently through Day 86 (3.03 ng/mL) (FIG. 3).

Figure 4:
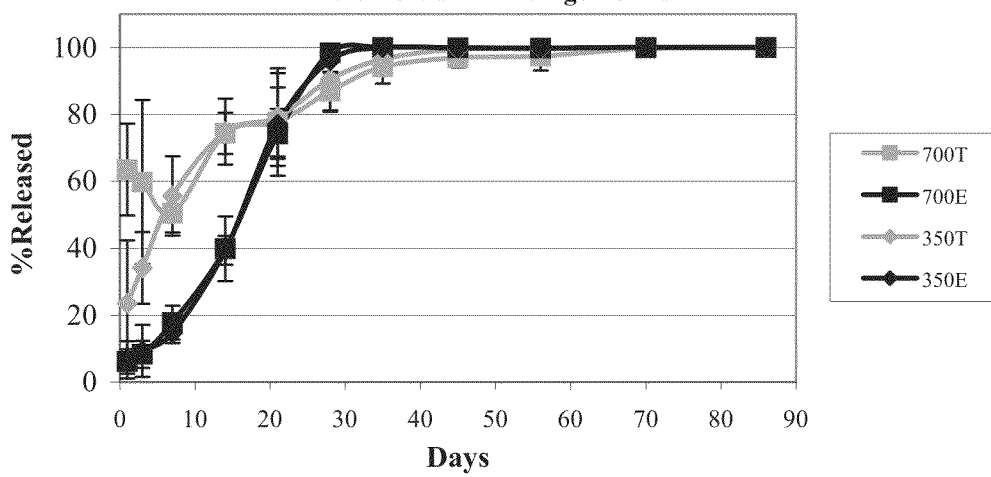
FIG. 4 is a graph showing cumulative percent of dexamethasone released into the vitreous humor over a period of 84 days for two tabletted implants (350 μg or 700 μg of dexamethasone) and for two extrusion formed implants (350 μg or 700 μg of dexamethasone.

The percent of dexamethasone released for each dosage form at each dose level was determined by assaying the section of the vitreous humor containing the DEX PS DDS remnants. Overall, the extruded dosage form provided a more consistent release of dexamethasone as evidenced by the lower standard deviations over the sampling period. For both dosage forms and dose levels, the mean percent of dexamethasone released by Day 35 was >90% (FIG. 4).

In the treated right eye, measurable concentrations of dexamethasone were found in the aqueous humor for both dosage forms and both dose levels at most time points up to Day 28, with peak mean aqueous humor concentrations paralleling peak mean vitreous humor concentrations. However, at most time points, peak mean plasma concentrations of dexamethasone were below, at or slightly above the limit of quantification (1.00 ng/mL). In the vitreous and aqueous humor of the control eyes dexamethasone content was generally below the limit of quantification.

Polymer matrix dissolution was evaluated in each group of animals at necropsy. Complete dissolution of the polymer matrix was observed at approximately 3 months in 58% of the animals receiving the extruded dosage form, and in 17% of the animals receiving the tablet dosage form, suggesting improved polymer matrix dissolution for the extruded dosage form.

In a subset of 24 animals, polymer matrix dissolution was assessed weekly. For the extruded dosage form, significant dissolution (1-24% remaining) had occurred in all but one eye by Day 46. Similarly, for the tablet dosage form, significant dissolution had occurred in all eyes by Day 57. Complete polymer matrix dissolution was observed by approximately 5 months for 67% of the extruded dosage form group and for 58% of the tablet dosage form group.

In summary, both dosage forms released an equivalent dose of dexamethasone, i.e., either 350 µg or 700 µg, over approximately 35 days, but achieved peak concentrations at different time points during the release period. Gradual, less variable release of dexamethasone, and more rapid dissolution of the polymer matrix were observed with the extruded dosage form.

Example 6

Extended Treatment of Macular Edema with an Intravitreal Dexamethasone Implant

An experiment was carried out with a biodegradable drug delivery system for implanting into the vitreous of the eye and release of dexamethasone (referred to hereafter as a "DEX PS DDS"). Such an implant can be used for the treatment of ocular conditions, such as macular edema.

Implants made according to the methods of Examples 1 and 2 were used. These implants form an intravitreal drug delivery system, which can be referred to as a Dexamethasone Posterior Segment Drug Delivery System (DEX PS DDS®), can deliver a 350 µg or 700 µg dose of dexamethasone intravitreally over approximately 35 days, allowing for a lower total dose and sustained drug levels to the target areas. DEX PS DDS is composed of dexamethasone homogeneously dispersed into a biodegradable matrix of copolymers of lactic acid and glycolic acid, PLGA (poly [lactic-glycolic] acid), a material commonly used in medical devices such as absorbable sutures. Dexamethasone is released gradually into the back of the eye over a period of approximately 35 days. The DEX PS DDS does not need to be removed since the copolymer dissolves completely over time.

By effectively delivering a sustained release anti-inflammatory drug intravitreally, DEX PS DDS can offer patients and clinicians a valuable new therapeutic option in the treatment of persistent macular edema that has persisted despite intervention, while reducing the potential for side-effects typically observed from steroid administration through other routes of delivery (e.g. systemic, etc.).

The objective of the experiment was to compare the safety and efficacy of two doses of DEX PS DDS (350 µg and 700 µg) versus observation (i.e. patients in which no implant was used) in the treatment of persistent macular edema (PME) persisting at least 90 days after laser treatment or after 90 days of medical management by a physician. Patients with PME associated with diabetic retinopathy, uveitis, retinal vein occlusion, and Irvine-Gass Syndrome were in the experiment.

A total of 306 patients, ages≥12 years old, with persistent macular edema associated with diabetic retinopathy, uveitis, branch retinal vein occlusion (BRVO), central retinal vein occlusion (CRVO) or Irvine-Gass Syndrome, persisting for at least 90 days following treatment were part of this 180-day study. At baseline, each patient provided written informed consent and a complete medical history including ocular history and prior medications (within the last 30 days). Potential study participants underwent measurements of best-corrected visual acuity (BCVA) based on ETDRS and intraocular pressure (IOP), and were examined for clinical signs of anterior chamber cells, anterior chamber flare, anterior vitreous cells, cataract, vitreal haze/retinal obscuration, vitreous/retinal hemorrhage, retinal detachment/tear and macular edema. Patients also underwent fluorescein angiography, fundus photography, and optical coherence tomography. Diabetic patients were tested for $HbA_{1c}$ and pre-menopausal women underwent urine pregnancy testing. For the purposes of this experiment persistent macular edema was defined as retinal thickening at the center of the fovea, visual acuity equal to or worse than 20/40, and angiographic evidence of leakage in the perifoveal capillary network.

After signing the informed consent form and determination of eligibility, patients were randomly assigned to treatment with 350 µg DEX PS DDS, or 700 µg DEX PS DDS, or observation.

DEX PS DDS (350 µg or 700 µg dexamethasone) was surgically implanted in the study eye of patients in the two active treatment groups. Insertion was performed through an incision in the pars plana inferotemporally, unless contraindicated during surgery by the Investigator. After closure, the suture knot was buried and subconjunctival and topical antibiotics were used prophylactically. If the delivery system became contaminated or damaged prior to insertion, it was replaced with a new, sterile system.

Visual Acuity

The visual acuity of patients in this study was measured according to the standard procedure developed for the Early Treatment Diabetic Retinopathy Study (ETDRS) and adapted for the Age-Related Eye Disease Study Protocol (AREDS) and this study. Visual acuity testing was required at a distance of 4-meters and, for subjects with sufficiently reduced vision, at 1-meter. ETDRS Charts 1 and 2 were used for testing the right and left eye, respectively, and Chart R was used for refraction.

Contrast Sensitivity

Contrast sensitivity, the ability of the eye to discern subtle degrees of contrast and size, is a sensitive measure of visual function which can be affected by the presence of retinal disease. Contrast sensitivity testing was performed as an additional measure of visual function using standardized, preprinted charts and standardized photopic and mesopic illumination by certified examiners. The outcome was measured as the lowest level of contrast at which a patient could distinguish pattern size displayed using a sine-wave contrast sensitivity vision test.

Fluorescein Angiography

Fluorescein angiography was conducted prior to randomization to provide angiographic evidence of leakage involving the perifoveal capillary networks and at select follow-up visits to assess anatomical improvement in macular edema. A central reading laboratory, FPRC (Fundus Photograph Reading Center, Madison, Wis.), was used to perform all readings. Readers were masked to patient treatment assignments.

Fundus Photography

Fundus photography was performed to assess macular thickness, an anatomical measure of macular edema, using standard techniques by certified photographers at each site. The photographs were assessed by masked readers at a central reading laboratory (FPRC).

Optical Coherence Tomography

Optical coherence tomography (OCT) is a laser-based non-invasive, diagnostic system providing high-resolution images of the retina (10 µm). Macular thickness, an anatomical indicator of macular edema, was assessed by a central reading laboratory (FPRC) from images obtained at Baseline and select follow-up visits. Readers were masked to patient treatment assignments.

Schedule of Exams

Patients, including both treatment groups and the observation group, were assessed according to the following schedule:

BCVA by ETDRS (Baseline, Days 7, 30, 60, 90, 180 or Early Termination);

Contrast sensitivity (Baseline, Days 30, 60, 90 or Early Termination);

Intraocular pressure (Baseline, Days 1, 7, 30, 60, 90, 180 or Early Termination);

Slit lamp biomicroscopy with fundus contact lens (Baseline, Days 1, 7, 30, 60, 90 or Early Termination) for clinical signs of macular edema;

Slit lamp assessment (Baseline, Days 1, 7, 30, 60, 90, 180 or Early Termination) for anterior chamber cells, anterior chamber flare, anterior vitreous cells, and cataract(s);

Indirect ophthalmoscopy (Baseline, Days 1, 7, 30, 60, 90, 180 or Early Termination) for vitreal haze/retinal obscuration, vitreous/retinal hemorrhage, retinal detachment/tear. DEX PS DDS was observed on Days 30, 60, 90, 180 or Early Termination only (with scleral depression);

Fluorescein angiography (Baseline, Days 30, 90 or Early Termination);

Fundus photography (Baseline, Day 0 [DEX PS DDS-treated group only if deemed necessary] Day 1 [Observation Group only if deemed necessary], Days 30, 60, 90 or Early Termination);

Optical coherence tomography (OCT) for macular thickness quantification at clinical sites where test available (Baseline, Days 30, 90 or Early Termination);

Vital signs: blood pressure (Baseline, Days 1, 7, 30, 60, 90);

$HbA_{1c}$—Baseline, Days 30, 60, 90 or Early Termination (if diabetic).

Efficacy

The primary efficacy parameter was BCVA (by ETDRS) improvement at the Day 90 follow-up visit. The BCVA improvement rate was defined as the proportion of subjects who had 2 lines or more improvement from baseline.

Secondary efficacy parameters were:

BCVA improvement at the Day 30 and Day 60 follow-up visits from baseline;

Mean change in the BCVA in Log MAR (log of the minimum angle of resolution) at the Day 30, Day 60, and Day 90 follow-up visits from baseline;

Mean change in measurements based on the contrast sensitivity evaluation performed at the Day 30, Day 60 and Day 90 follow-up visits from baseline;

Mean change in measurements based on the fluorescein angiography evaluation performed at the Day 30 and Day 90 follow-up visits;

Mean change in measurements based on the fundus photography evaluation performed at the Day 30, Day 60 and Day 90 follow-up visits;

Mean change in the retinal thickness in 1-mm diameter center subfield based on the OCT evaluation at the Day 30 and Day 90 follow-up visits from baseline;

Mean change in measurements based on the clinical signs of persistent macular edema (PME) evaluation by slit lamp biomicroscopy performed at the Day 1, Day 7, Day 30, Day 60 and Day 90 follow-up visits;

Mean change in BCVA from Baseline to the Day 7, 30, Day 60 and Day 90 follow-up visits.

Results

A total of 315 patients with persistent macular edema (PME) were enrolled in the clinical study. One hundred five (105) patients were assigned to each of the three study groups, i.e., DEX PS DDS 350 µg, DEX PS DDS 700 µg, or observation only. Five patients assigned to the 350 µg treatment group and 4 patients assigned to the 700 µg treatment group withdrew before DEX PS DDS treatment was initiated due to a change in eligibility status since randomization or personal reasons and therefore were not included within the intent-to-treat population. Of the total intent-to-treat (ITT) study population (n=306), 51.3% of the patients were male and 48.7% were female, with 9 patients less than 40 years of age (2.9%), 119 patients in the 40 to 65 year range (38.9%), and 178 patients over 65 years of age (58.2%). The mean age was 66 years (SD=11.9) consistent with the greater prevalence of eye pathologies among older adults. The majority of patients were Caucasian (77.8%), with the remaining patients from the following ethnic groups: Black (7.5%), Hispanic (11.1%), Asian (2.6%), and Native American (1.0%).

Improved Visual Acuity

As shown in Table 1, use of both the 350 µg and the 700 µg DEX PS DDS resulted in visual acuity improvement of two or more lines in BCVA at Day 30, Day 90 and as well at Day 180. All the visual acuity improvement percentages shown in Table 1 were greater at each time (Day 90 and Day 180) and for each type of implant (350 µg and 700 µg) than was the visual acuity improvement percentage seen in the patients in the observation group.

Thus, it was demonstrated that use of an implant according to the method set forth herein permits a patients' visual acuity to improve and that the patient's improved visual acuity can be retained for a period of time long after the implant has released all the dexamethasone.

TABLE 1

Improved Visual Acuity 30, 60 and 90 Days after Placement of Intravitreal Implant

|  | DEX PS DDS 350 mg (n = 100) | DEX PS DDS 700 mg (n = 101) | Observation group (n = 105) |
|---|---|---|---|
| Day 30 BCVA n | 89 | 93 | 94 |
| ≥2 line gain | 21% | 22% | 16% |
| ≥3 line gain | 9% | 13% | 6% |
| Day 90 BCVA n | 92 | 98 | 100 |
| ≥2 line gain | 26% | 37% | 19% |
| ≥3 line gain | 13% | 16% | 9% |
| Day 180 BCVA n | 92 | 98 | 100 |
| ≥2 line gain | 27% | 36.% | 19% |
| ≥3 line gain | 13% | 19% | 8% |

Improved Visual Contrast Sensitivity

Change in contrast sensitivity, an assessment of visual function, was measured at baseline, and at Days 30, 60, and 90 using a sine-wave contrast sensitivity vision test. As shown by Table 2, the LOCF mean Contrast Sensitivity Score at 1.5 cpd (Patch A) was higher in patients in both DEX PS DDS treatment groups compared to the observation group at Day 60 (p<0.001) and Day 90 (p=0.006). The improvement appeared first among those in the 350 µg treatment group at Day 30 (p=0.028), but by Day 60 patients in both the 350 µg and the 700 µg treatment groups experienced significant visual function improvement (p<0.001 and p=0.011, respectively). This improvement was maintained to Day (p=0.004 and p=0.010, respectively). A similar treatment effect (data not shown) on LOCF mean Contrast Sensitivity Score at 3.0 cpd (Patch B) was observed for both the 350 µg and the 700 µg DEX PS DDS treatment groups, compared to the observation group, by Day 60 (p<0.001 and p=0.030, respectively), and continued through Day 90 for both treatment groups (p=0.021 and p=0.007, respectively).

Thus, it was demonstrated that use of an implant according to the method set forth herein permits a patients' visual contrast sensitivity to improve and that the patient's improved visual contrast sensitivity can be retained for a period of time long after the implant has released all the dexamethasone.

TABLE 2

Improved Visual Contrast Sensitivity 30 Days, 60 Days and 90 Days after Placement of Intravitreal Implant

|  | Treatment Group | | |
| --- | --- | --- | --- |
|  | DEX PS DDS 350 mg | DEX PS DDS 700 mg | Observation Group |
| Change from Baseline at Day 30 | 0.89 | 0.56 | 0.38 |
| Change from Baseline at Day 60 | 1.21 | 0.80 | 0.13 |
| Change from Baseline at Day 90 | 1.02 | 0.97 | 0.33 |

Improved (Decreased) Retinal Thickness (OCT)

Change in retinal thickness, an anatomical measure of macular edema, was assessed by Optical Coherence Tomography (OCT) at Days 30 and 90. Patients who had baseline and at least one follow-up evaluation were included in this analysis. As shown by Table 3, the LOCF average retinal thickness score was improved by Day 30 for both treatment groups as compared to the observation group (p<0.001 for 350 µg and 700 µg DEX PS DDS). This improvement continued to Day 90 for both treatment groups, with a significantly greater decrease in retinal thickness in the 700 µg treatment group (p<0.001) and the 350 µg treatment group (p=0.016) compared to the observation group.

Thus, it was demonstrated that use of an implant according to the method set forth herein permits a patients' aberrant retinal thickness to improve and that the patient's improved (decreased) retinal thickness can be retained for a period of time long after the implant has released all the dexamethasone.

TABLE 3

Improved (Decreased) Retinal Thickness as Measured by Optical Coherence Tomography (OCT) 30 Days and 90 Days after Placement of Intravitreal Implant

|  | Treatment Group | | |
| --- | --- | --- | --- |
| Retinal Thickness (µm) | DEX PS DDS 350 mg | DEX PS DDS 700 mg | Observation Group |
| Change from Baseline at Day 30 | −102.96 | −157.11 | 12.73 |
| Change from Baseline at Day 90 | −63.08 | −147.20 | 9.54 |

Improved (Decreased) Retinal Vessel Leakage

Categorical improvement in leakage of the retinal vasculature, an anatomical measure of macular edema, was assessed by fluorescein angiography at baseline, Day 30 and at Day 90. Patients who had baseline and at least one follow-up evaluation were included in the analysis. As shown by Table 4, LOCF fluorescein leakage scores improved as compared to the observation group for patients in both treatment groups by Day 30. By Day 90, fluorescein leakage for both DEX PS DDS treatment groups was significantly improved over the observation group (700 µg; p<0.001 and 350 mg; p=0.001).

Thus, it was demonstrated that use of an implant according to the method set forth herein permits a patients' retinal blood vessel leakage to decrease and that this improvement can be retained for a period of time long after the implant has released all the dexamethasone.

TABLE 4

Improved (Decreased) Retinal Blood Vessel Leakage as Measured by Fluorescein Angiography 30 Days and 90 Days after Placement of Intravitreal Implant

| Improvement in | Treatment Group | | |
| --- | --- | --- | --- |
| Maximum Fluorescein Leakage | DEX PS DDS 350 mg | DEX PS DDS 700 mg | Observation Group |
| Change from Baseline at Day 30 | | | |
| ≥2 levels better | 17% | 28% | 6% |
| ≥3 levels better | 11% | 22% | 4% |
| Change from Baseline to Day 90 | | | |
| ≥2 levels better | 20% | 34% | 4% |
| ≥3 levels better | 16% | 25% | 1% |

Improved (Decreased) Retinal Thickness (Fundus Photography)

Categorical improvement in retinal thickness was also assessed by fundus photography at baseline, Day 30 and at Day 90. Patients who had baseline and at least one follow-up evaluation were included in the analysis. As shown by Table 5, at Day 30, retinal thickness scores for both DEX PS DDS treatment groups were significantly improved over the observation group (700 µg; p<0.001 and 350 mg; p=0.031) By Day 90, the 700 µg treatment group continued to show statistical significance in improvement of LOCF retinal thickness scores (p<0.001).

Thus, it was demonstrated that use of an implant according to the method set forth herein permits a patients' aberrant retinal thickness to improve and that the patient's improved (decreased) retinal thickness can be retained for a period of time long after the implant has released all the dexamethasone.

TABLE 5

Improved (Decreased) Retinal Thickness as Measured by Fundus Photography 30 Days and 90 Days after Placement of Intravitreal Implant

| Improved Retinal Thickness | Treatment Group | | |
|---|---|---|---|
| | DEX PS DDS 350 mg | DEX PS DDS 700 mg | Observation Group |
| Change from Baseline at Day 30 | | | |
| ≥2 levels better | 13% | 23% | 2% |
| ≥3 levels better | 6% | 14% | 1% |
| Change from Baseline at Day 90 | | | |
| ≥2 levels better | 16% | 30% | 4% |
| ≥3 levels better | 10% | 24% | 2% |

Intraocular Pressure

Intraocular pressure (IOP) was recorded on days 1, 7, 30, 60, 90 and the 180. Over the course of the study 22 events of elevation in IOP≥25 mm Hg were noted in 17 patients receiving the 350 µg treatment and 22 events in 15 patients receiving the 700 µg treatment. No event of elevation in IOP≥25 mmHg was noted in the observation group. Differences in IOP of ≥25 mm Hg between the 700 µg treatment group (n=7) and the observation group were significant at the day 180 visit only (p=0.014). No statistical difference was seen at any time interval for the 350 µg treatment group as compared to the observation group.

Of the 7 patients with elevated IOP at day 180, one patient had an ocular history of glaucoma in both eyes at the baseline visit. A second patient did not receive medication and the elevated IOP resolved the same day.

As shown by Table 6, increases of IOP 10 mm Hg from baseline occurred in a small number of eyes in all three groups. At no time was there a statistical difference between the 350 µg group and the observation group. When the 700 µg treatment group was compared to the observation group, statistical difference was seen at Day 60 only (p=0.044).

Prior to the present invention is believed that intravitreal administration of a steroid would cause a much more significant increase in intraocular pressure than was observed in the present study. See e.g. Wingate R., et al., *Intravitreal triamcinolone and elevated intraocular pressure*, Aust & New Zea. J of Ophthalmology 27(6):431-2, December 1999; Gillies M., et al., *Safety of an intravitreal injection of triamcinolone*, Arch Ophthalmol vol 122, 336-340 March 2004, and; Jonas J. et al., *Intraocular pressure after intravitreal injection of triamcinolone acetonide*, Br. J. Ophthalmol 2003; 87: 24-27.

TABLE 6

Summary of Change from Baseline to Follow-up Visits in Intraocular Pressure ≥10 mmHg

| Study Group | | Follow-up Visit | | | | | |
|---|---|---|---|---|---|---|---|
| | | Day 1 | Day 7 | Day 30 | Day 60 | Day 90 | Day 180 |
| DEX PS DDS 350 mg | % of patients with Increase in IOP over baseline of >=10 mm Hg | 5 | 2 | 2 | 2 | 2 | 2 |
| DEX PS DDS 700 mg | % of patients with Increase in IOP over baseline of >=10 mm Hg | 5 | 3 | 1 | 3 | 2 | 6 |
| Observation Group | % of patients with Increase in IOP over baseline of >=10 mm Hg | 3 | 4 | 2 | 0 | 1 | 1 |

Cataract Development

There was no significant difference in cataract development between treatment groups at any time point. Over 60% of patients in all three study groups had a cataract present at baseline. As shown by Table 7 there was no significant new cases of cataract.

TABLE 7

New Cases of Cataract Observed During the Study

| Treatment Group | | Number of New Cataracts by Type of Cataract | | |
|---|---|---|---|---|
| | | Cortical | Nuclear | Subcapsular |
| 350 mg DEX PS DDS | (n = 100) | 0 | 1 | 0 |
| 700 mg DEX PS DDS | (n = 101) | 1 | 1 | 1 |
| Observation Group | (n = 105) | 1 | 1 | 1 |

Prior to the present invention is was believed that intravitreal administration of a steroid would cause a much more significant increase in cataracts than was observed in the present study. See e.g. Gillies M., et al., *Safety of an intravitreal injection of triamcinolone*, Arch Ophthalmol vol 122, 336-340 March 2004.

Implant Dissolution and Location

DEX PS DDS dissolution and location were monitored by slit lamp examination at all visits over the course of the study. DDS dissolution was quantified based on a scale of absent, trace present, <25%, <50%, ≤100% or >100% present. No differences were observed between the dissolution rate of the 350 µg and the 700 µg treatment groups. At the Day 180 visit, 68.1% of patients in the 350 µg group and 65.3% of patients in the 700 mg group had no visible presence of residual DEX PS DDS. Of the remaining patients, most had only trace to ≤25% amounts of residual DEX PS DDS remaining by the Day 180 visit. There was no significant difference in the location of the DEX PS DDS between the two treatment groups at any time during the course of the study.

The DEX PS DDS was found to be stable upon placement. No significant migration of the DEX PS DDS was noted for either the 350 µg or 700 µg treatment group. Categorical analysis across all DEX PS DDS locations showed no significant difference at any time interval using Fisher's Exact test.

To conclude the safety and efficacy of two doses of Dexamethasone Posterior Segment Drug Delivery System (DEX PS DDS) versus observation for the treatment of persistent macular edema (PME) was tested in a Phase 2, prospective, randomized, multicenter, dose-ranging, controlled clinical trial. A total of 315 patients, ≥15 years of age, with PME associated with diabetic retinopathy, uveitis, branch retinal vein occlusion (BRVO), central retinal vein occlusion (CRVO) or Irvine-Gass Syndrome present for at least 90 days despite prior intervention were enrolled in this 180-day study. Patients were randomized in a 1:1:1 ratio to one of three study groups: 700 µg DEX PS DDS, 350 µg DEX PS DDS or observation. The intent-to-treat (ITT) population consisted of 306 patients who were balanced between the three study groups in terms of patient sex, age, race, baseline etiology and duration of initial onset and duration of persistent macular edema.

Example 7

Extended Treatment of Ocular Conditions with Various Active Agents

An implant can be formulated with various active agents following the procedures in Examples 1 and 2. These implants can provide an extended therapeutic treatment of an ocular condition, that is a therapeutic affect during a period of time after release of all of the active agent from the implant and during which there is no longer a therapeutic amount of the active agent present at the ocular site at which the implant was placed. Thus, an implant can be prepared containing a nonsteroidal anti-inflammatory agent, such as ketorolac ketorolac (available from Allergan, Irvine, Calif. as ketorolac tromethamine ophthalmic solution, under the tradename Acular). Thus, for example, a ketorolac ketorolac extended therapeutic treatment implant can be implanted into an ocular site (i.e. into the vitreous) of a patient with an ocular condition for a desired extended therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using the procedure such as trocar implantation. The implant can release a therapeutic amount of the active agent to provide and retain a therapeutic effect for an extended period of time to thereby treat a symptom of an ocular condition.

Such an implant to provide an extended therapeutic treatment of an ocular condition can also be prepared containing a steroid, such an anti-angiogenesis steroid, such as an anecortave, as the active agent.

VEGF (Vascular Endothelial Growth Factor) (also known as VEGF-A) is a growth factor which can stimulate vascular endothelial cell growth, survival, and proliferation. VEGF is believed to play a central role in the development of new blood vessels (angiogenesis) and the survival of immature blood vessels (vascular maintenance). Tumor expression of VEGF can lead to the development and maintenance of a vascular network, which promotes tumor growth and metastasis. Thus, increased VEGF expression correlates with poor prognosis in many tumor types. Inhibition of VEGF can be an anticancer therapy used alone or to complement current therapeutic modalities (e.g., radiation, chemotherapy, targeted biologic therapies).

VEGF is believed to exert its effects by binding to and activating two structurally related membrane receptor tyrosine kinases, VEGF receptor-1 (VEGFR-1 or flt-1) and VEGFR-2 (flk-1 or KDR), which are expressed by endothelial cells within the blood vessel wall. VEGF may also interact with the structurally distinct receptor neuropilin-1. Binding of VEGF to these receptors initiates a signaling cascade, resulting in effects on gene expression and cell survival, proliferation, and migration. VEGF is a member of a family of structurally related proteins (see Table A below). These proteins bind to a family of VEGFRs (VEGF receptors), thereby stimulating various biologic processes. Placental growth factor (PlGF) and VEGF-B bind primarily to VEGFR-1. PlGF modulates angiogenesis and may also play a role in the inflammatory response. VEGF-C and VEGF-D bind primarily to VEGFR-3 and stimulate lymphangiogenesis rather than angiogenesis.

TABLE A

| VEGF Family Members | Receptors | Functions |
|---|---|---|
| VEGF (VEGF-A) | VEGFR-1, VEGFR-2, neuropilin-1 | Angiogenesis Vascular maintenance |
| VEGF-B | VEGFR-1 | Not established |
| VEGF-C | VEGF-R, VEGFR-3 | Lymphangiogenesis |
| VEGF-D | VEGFR-2, VEGFR-3 | Lymphangiogenesis |
| VEGF-E (viral factor) | VEGFR-2 | Angiogenesis |
| PlGF | VEGFR-1, neuropilin-1 | Angiogenesis and inflammation |

An extended therapeutic effect implant system to treat an ocular condition can contain as active agent a compound with acts to inhibit formation of VEGF or to inhibit the binding of VEGF to its VERFR. The active agent can be, for example, ranibizumab (rhuFab V2) (Genentech, South San Francisco, Calif.) and the implant(s) can be made using the method of Example 1 or the method of Example 2, but with use of ranibizumab as the active agent, instead of dexamethasone. Ranibizumab is an anti-VEGF (vascular endothelial growth factor) product which may have particular utility for patients with macular degeneration, including the wet form of age-related macular degeneration. The implant can be loaded with about 100-300 µg of the ranibizumab.

Pegaptanib is an aptamer that can selectively bind to and neutralize VEGF and may have utility for treatment of, for example, age-related macular degeneration and diabetic macular edema by inhibiting abnormal blood vessel growth and by stabilizing or reverse blood vessel leakage in the back of the eye resulting in improved vision. An extended therapeutic treatment implant can be made with of pegaptanib sodium (Macugen; Pfizer Inc, New York or Eyetech Pharmaceuticals, New York) as the active agent by loading about 1 mg to 3 mg of Macugen according to the Example 1 or 2 method.

The pegaptanib sodium extended release implant system can be implanted into an ocular region or site (i.e. into the vitreous) of a patient with an ocular condition for a desired extended therapeutic effect.

An extended treatment bioerodible intraocular implant for treating an ocular condition, such as an ocular tumor can also be made as set forth in this Example using about 1 mg of the VEGF Trap compound available from Regeneron, Tarrytown, N.Y.

An extended therapeutic treatment implant treat an ocular condition can contain a beta-adrenergic receptor antagonist (i.e. a "beta blocker) such as levobunolol, betaxolol, carteolol, timolol hemihydrate and timolol. Timolol maleate is commonly used to treat of open-angle glaucoma. Thus, an extended therapeutic treatment bioerodible implant containing timolol maleate (available from multiple different suppliers under the trade names Timoptic, Timolol or Loptomit) as the active agent can be made using the method of Example 1 or the method of Example 2, but with use of timolol maleate instead of dexamethasone. Thus, about 50 µg of the timolol maleate can be loaded into each of the three implants prepared according to the Example 1 or method.

The timolol extended release implant system can be implanted into an ocular region or site (i.e. into the vitreous) of a patient with an ocular condition for a desired extended therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma.

An extended therapeutic treatment implant system can be used to treat an ocular condition can contain a prostamide. Prostamides are naturally occurring substances biosynthesized from anandamide in a pathway that includes COX2. Bimatoprost (Lumigan) is a synthetic prostamide analog chemically related to prostamide F. Lumigan has been approved by the FDA for the reduction of elevated intraocular pressure (IOP) in patients with open-angle glaucoma or ocular hypertension who are intolerant of or insufficiently responsive to other IOP-lowering medications. Lumigan is believed to lower intraocular pressure by increasing the outflow of aqueous humor.

Thus, an extended therapeutic treatment bioerodible implant containing Lumigan (Allergan, Irvine, Calif.) as the active agent can be made using the method of Example 1 or the method of Example 2, but with use of Lumigan instead of dexamethasone. Thus, about 100 µg of Lumigan can be loaded into each of the three implants prepared according to the Example 1 or 2 method.

The Lumigan extended therapeutic effect implant can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma.

An extended therapeutic treatment implant can be used to treat an ocular condition wherein the implant contains as the active agent an alpha-2 adrenergic receptor agonist, such as clonidine, apraclonidine, or brimonidine. Thus, an extended release bioerodible implant system containing brimonidine (Allergan, Irvine, Calif., as Alphagan or Alphagan P) as the active agent can be made using the method of Example 1 or the method of Example 2, but with use of Alphagan instead of dexamethasone. Thus, about 50 µg of Alphagan can be loaded into an implant prepared according to the Example 1 or 2 method.

The brimonidine extended therapeutic treatment implant can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma.

An extended therapeutic effect implant used to treat an ocular condition can contain a retinoid such as an ethyl nicotinate, such as a tazarotene. Thus, an extended release bioerodible implant system containing tazarotene (Allergan, Irvine, Calif.) as the active agent can be made using the method of Example 1 or the method of Example 2, but with use of tazarotene instead of dexamethasone. Thus, about 100 µg to 300 µg of tazarotene can be loaded into each of the three implants prepared according to the Example 1 or 2 method.

The tazarotene extended therapeutic treatment implant can be implanted into an ocular region or site (i.e. into the vitreous) of a patient with an ocular condition for a desired therapeutic effect.

Generally, tyrosine kinase inhibitors are small molecule inhibitors of growth factor signaling. Protein tyrosine kinases (PTKs) comprise a large and diverse class of proteins having enzymatic activity. The PTKs play an important role in the control of cell growth and differentiation. For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular). The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogene 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci. 90: 10705-09; Kim, et al, 1993, Nature 362: 841-844), RNA ligands (Jellinek, et al, Biochemistry 33: 10450-56); Takano, et al, 1993, Mol. Bio. Cell 4:358 A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330,992; Mariani, et al, 1994, Proc. Am. Assoc. Cancer Res. 35: 2268).

An extended therapeutic treatment implant to treat an ocular condition can contain a tyrosine kinase inhibitor (TKI) such as a TKI set forth in published U.S. patent application 2004 00019098 (available from Allergan, Irvine, Calif.) as the active agent can be made using the method of Example 1 or the method of Example 2, but with use of a TKI instead of dexamethasone. Thus, about 100 µg of a TKI can be loaded into each of the three implants prepared according to the Example 1 or 2 method.

The TKI extended therapeutic effect implant can be implanted into an ocular region or site (i.e. into the vitreous) of a patient with an ocular condition for a desired extended therapeutic effect.

It is believed that overstimulation of the N-methyl-D-aspartate (NMDA) receptor by glutamate is implicated in a variety of disorders. Memantine is an NMDA antagonist which can be used to reduce neuronal damage mediated by the NMDA receptor complex. Memantine is available from Merz Pharmaceuticals, Greensboro, N.C. under the trade name Axura. An extended release implant system can be used to treat an ocular condition. The implant can contain an NMDA antagonist such as memantine. Thus, an extended therapeutic treatment bioerodible implant containing memantine as the active agent can be made using the method of Example 1 or the method of Example 2, but with use of memantine instead of dexamethasone. Thus, about 400 µg of memantine can be loaded into each of the three implants prepared according to the Example 1 or 2 method.

The memantine extended release implant system can be implanted into an ocular region or site (i.e. into the vitreous) of a patient with an ocular condition for a desired extended therapeutic effect.

Certain estratropones have anti-angiogenesis, anti-neoplastic and related useful therapeutic activities. An extended therapeutic treatment implant can contain an estratropone such as 2-methoxyestradiol (available from Entremed, Inc., of Rockville, Md. under the tradename Panzem). Thus, an extended therapeutic treatment bioerodible implant containing memantine as the active agent can be made using the method of Example 1 or the method of Example 2, but with use of 2-methoxyestradiol instead of dexamethasone. 2-methoxyestradiol can be used as a small molecule angiogenic inhibitor to block abnormal blood vessel formation in the back of the eye. Thus, about 400 µg of 2-methoxyestradiol can be loaded into each of the three implants prepared according to the Example 1 or 2 method.

The 2-methoxyestradiol extended release implant system can be implanted into an ocular region or site (i.e. into the vitreous) of a patient with an ocular condition for a desired extended therapeutic effect.

Using the same methodology set forth in Examples 1 and 2, additional extended therapeutic treatment implants can be prepared wherein the active agent is, for example, an agent to treat intravitreal hemorrhage (such as Vitrase, available from Ista Pharmaceuticals), an antibiotic (such as cyclosporine, or gatifloxacin, the former being available from Allergan, Irvine, Calif. under the tradename Restasis and the later from Allergan under the tradename Zymar), ofloxacin, an androgen, epinastine (Elestat, Allergan, Irvine, Calif.), or with a combination of two or more active agents (such as a combination in a single extended release implant of a prostamide (i.e. bimatoprost) and a best blocker (i.e. timolol) or a combination of an alpha 2 adrenergic agonist (i.e. brimonidine) and a beta blocker, such as timolol) in the same extended delivery system. A method using an implant within the scope of the present invention can be used in conjunction with a photodynamic therapy or laser procedure upon an eye tissue.

Example 8

Remnant Effect of DEX-PS-DDS on VEGF-Induced Retinopathy in Monkeys

Six cynomolgus monkeys, each weighing between 3-4.5 kg, were used for these studies. Animals were maintained under anesthesia during all procedures. Briefly, monkeys were first sedated with 10 mg/kg ketamine, administered intramuscularly and removed from their cage. Animals were intubated with an appropriately sized and sealed endotracheal tube, immobilized with intravenous administration of 0.45 mg/kg Zemuron® (rocuronium bromide, a neuromuscular blocking agent) and placed on a ventilation-assist device (Engler 1000) with 100% oxygen gas.

The animals' pupils were dilated with 1 drop of 2.5% phenylephrine and 1 drop of 1% tropicamide. End tidal $CO_2$, $SpO_2$ and heart rate were recorded at 10-minute intervals to monitor ventilation efficiency and ensure stability of the animal's physiological status. If necessary during the course of the experiment, a supplemental dose of 0.15 mg/kg Zemuron® was administered to maintain and insure the immobility of the animal.

Corneal hydration was maintained by ensuring that the eyelids remained closed when no imaging was being performed; during imaging procedures a speculum was used to prop the eyelids of the sampled eye open and the cornea regularly bathed with 0.9% physiological saline. The eyelid speculum was removed immediately following conclusion of imaging procedures and the eyelids manually closed.

Animal recovery following conclusion of the endpoint measurements was carefully monitored. The time from first eyelid movement to the ambulatory state typically ranges from 20 minutes to 1 hour. Although intravenous administration of 0.022 mg/kg atropine and 0.045 mg/kg Neostigmine (an anticholinesterase agent) reduces recovery time to less than 10 minutes, it is preferable and may be safer to the animals' well being to allow them to recover without drug intervention.

Animals were separated into two groups of three, one group receiving a 700 µg intravitreal dexamethasone implant (DEX-PS-DDS) administered via the infero-temporal pars plana region using a 22-gauge applicator into the left (OS) eye, and the other group treated with an injection of PS-DDS lacking dexamethasone, OS. Generally, all significant dexamethasone is released from the DDS implant within approximately 30 days.

At 1 week, 7 weeks and 15 weeks post-injection, 1.25 µg human vascular endothelial growth factor isoform 165 (VEGF h165) in a volume of 50 µl was injected OS with a 30-gauge needle 1-2 mm over the macula in both control and test groups in order to induce retinal changes such as those seen in conditions including macular degeneration and diabetic retinopathy.

Assessments of the following parameters were made pre-DEX-PS-DDS (or control) injection, before treatment with VEGF, and 7 days after each VEGF injection.

Seven days after each VEGF injection the following assessments were made:
a) measurement of anterior chamber flare (0-4 scale using slit lamp),
b) retinal vascular leak and dilation (0-3 scale using fluorescein angiograms),
c) foveal thickness (using Zeiss® Optical Coherence Tomography),
d) optic nerve cup volume (using Heidelberg Retinal Tomography) and
e) ERG (electroretinography) (using Espion® ColorDome®; electrophysiology system).

The results of this experiment showed that Dex-PS-DDS inhibited the development of VEGF-induced retinopathy throughout the 16-week experiment. Signs of disease, including anterior chamber flare, vascular dilation, and leakage of blood into the retina were consistently observed in the control group at the 2, and 16 week timepoints but were absent in the Dex-PS-DDS treated animals throughout the time period of the experiment.

Optic nerve head swelling in response to VEGF treatment in the control group caused a decrease in cup volume to approximately 15%-18% of the control eye; the cup volumes in the Dex DDS group at 2, 8 and 16 weeks were better preserved, having a cup volume of 64% (±15%), 75% (±4%) and 96% (±12%), that of the control eye at 2, 8, and 16 weeks, respectively.

The VEGF-induced foveal thickness was consistently greater in the control group: 150±9 µm, 462±181 µm, 968±270 µm at the 2, 8 and 16 week timepoints, respectively. Foveal thickness remained unchanged over time in the Dex-PS-DDS group, within a range of 133-137 µm out to 4 months.

VEGF injection resulting in reduced ERG amplitude over the course of the study in both groups, indicating somewhat reduced retinal function; however, the reductions were 2 to 5-fold less in the Dex-PS-DDS animals. In the control group, % of OS responses for b-wave at 1 cd·s/m² was 52% (±5%), 32% (±15%) and 10% (±10%) at the 2, 8 and 16 week timepoints, respectively. By contrast, in the Dex-PS-DDS group, the corresponding values were 103% (±3%), 87% (±13%), and 51% (±10%).

These results indicate that dexamethasone, intravitreally administered in a DDS device, can provide a therapeutic effect countering or resisting the at least one symptom of VEGF-induced retinopathy for a significant time after the dexamethasone has been released from the DDS implant. In a preferred embodiment the glucocorticoid has such a countering or resisting effect for at least 4 days following the release of all significant amounts of dexamethasone into the vitreous. In other embodiments the glucocorticoid has such a countering or resisting effect for at least 1 week, or at least 2 weeks, or at least 3 weeks, or at least 4 weeks, or at least 5 weeks, or at least 6 weeks, or at least 7 weeks, or at least 8 weeks, or at least 9 weeks, or at least 9 weeks, or at least 10 weeks, or at least 11 weeks, or at least 12 weeks following the release of all significant amounts of dexamethasone into the vitreous.

In another embodiment the present invention comprises a method of preventing the presentation of at least one symptom of a retinal disorder comprising administering to the vitreous of a mammal at risk of such presentation a glucocorticoid at a dosage effective to reduce the severity of such symptom in a different patient suffering from said retinal disorder, comprising administering said dosage to the vitreous of a patient's eye before the presentation of said at least one symptom.

Example 9

Remnant Effect after Intravitreal Invention of Triamcinolone Acetonide (TA)

An experiment was carried out which determined existence of a remnant effect (i.e. a therapeutic effect of the active agent when a therapeutic amount of the active agent was not longer present) of intravitreal triamcinolone. Six Dutch-belted rabbits were divided into two groups of three each. After standard pars plana vitrectomy, one group received 4 mg of the glucocorticoid triamcinolone acetonide (TA) in a 0.1 ml volume (Kenalog® 40), and the other group received 0.1 ml of a 5% PLGA (poly lactic/glycolic acid) solution. One minute later the TA or PLGA was removed with a subtotal vitrectomy and soft tip needle. Forty-eight hours after the surgery $VEGF_{165}$ (500 ng/50 µl) was injected intravitreally via a 29 gauge needle to induce retinal vasculopathy and assess a pharmacological action of any remnant effect of either TA or PLGA. Assessment of retinal color fundus imaging, fluorescein angiography (FA), and fluorometry was made upon VEGF administration and 48 hours following such administration to assess leak from the retina vasculature as a result of $VEGF_{165}$ administration, and the effect of either TA or PLGA on such leakage.

Less leakage was seen in the TA-treated group than in the PLGA group after 48 hours upon fluorescence angiography. Fluorophotometry "area under the curve" analysis showed a change from baseline of 3±65% in the TA group and 487±260% in the PLGA group. Thus, TA shows residual pharmacological activity 4 days following the procedure, i.e. a remnant effect.

All references, articles, patents, applications and publications set forth above are incorporated herein by reference in their entireties.

Accordingly, the spirit and scope of the following claims should not be limited to the descriptions of the preferred embodiments set forth above.

What is claimed is:

1. An ocular implant for treating an ocular condition comprising an active agent and a carrier associated with the active agent, wherein the carrier comprises a 30/10 w/w mixture of hydrophilic end PLGA and hydrophobic end PLGA and wherein the active agent is a prostamide and wherein the ocular implant is formed by an extrusion method.

2. The ocular implant of claim 1, wherein the prostamide is bimatoprost.

3. The ocular implant of claim 1, wherein the total weight of the ocular implant is between about 100 µg and about 2 mg.

4. The ocular implant of claim 1, wherein the implant is 60% by weight the active agent and 40% by weight the carrier.

5. The ocular implant of claim 1, wherein the implant is suitable for intravitreal implantation.

6. The ocular implant of claim 1, wherein the ocular condition is elevated intraocular pressure (IOP).

7. The ocular implant of claim 1, wherein the ocular condition is uveitis.

8. The ocular implant of claim 1, wherein the ocular condition is macular degeneration.

* * * * *